US010039567B2

(12) United States Patent
Esarey et al.

(10) Patent No.: US 10,039,567 B2
(45) Date of Patent: Aug. 7, 2018

(54) POWER OPERATED DERMATOME WITH SHIELDED ROTARY KNIFE BLADE

(71) Applicants: Bernard J. Esarey, Avon, OH (US); Jeffrey A. Whited, Amherst, OH (US)

(72) Inventors: Bernard J. Esarey, Avon, OH (US); Jeffrey A. Whited, Amherst, OH (US)

(73) Assignee: Exsurco Medical, Inc., Birmingham, OH (US)

( * ) Notice: Subject to any disclaimer, the term of this patent is extended or adjusted under 35 U.S.C. 154(b) by 154 days.

(21) Appl. No.: 13/842,224

(22) Filed: Mar. 15, 2013

(65) Prior Publication Data

US 2014/0074120 A1   Mar. 13, 2014

Related U.S. Application Data

(63) Continuation-in-part of application No. 13/606,836, filed on Sep. 7, 2012, now Pat. No. 9,592,076.

(51) Int. Cl.
*A61B 17/322* (2006.01)
*A61B 90/00* (2016.01)

(52) U.S. Cl.
CPC ...... *A61B 17/322* (2013.01); *A61B 2090/033* (2016.02)

(58) Field of Classification Search
CPC .............. A61B 17/322; A61B 17/3205; A61B 17/320758; A61B 2017/00761;
(Continued)

(56) References Cited

U.S. PATENT DOCUMENTS 3,197,808 A   8/1965 Mears
3,269,010 A   8/1966 Bettcher
(Continued)

FOREIGN PATENT DOCUMENTS

GB   1515047   6/1978

OTHER PUBLICATIONS

International Search Report dated Dec. 12, 2013 and Written Opinion of the International Searching Authority dated Dec. 12, 2013 for PCT International Application No. PCT/US2013/058133, filed Sep. 5, 2013. PCT International Application No. PCT/US2013/058133 corresponds to and claims priority from U.S. Appl. No. 13/606,836, filed Sep. 7, 2012. The present application is a continuation-in-part of and claims priority from U.S. Appl. No. 13/606,836. (10 pages) (Exhibit A).
(Continued)

*Primary Examiner* — Ryan J Severson
*Assistant Examiner* — Christian Knauss
(74) *Attorney, Agent, or Firm* — Tarolli, Sundheim, Covell & Tummino LLP

(57) ABSTRACT

A combination (2290) of an annular rotary knife blade (2300) and blade housing assembly (2400) for a power operated dermatome (2000). The rotary knife blade includes an inner wall (2310) defining an interior region (2301) and including a lower tissue-directing surface (2370) adjacent a cutting edge (2360) and a radially recessed upper portion (2380). The blade housing assembly includes a blade housing (2410) having a first end (2412) and an axially spaced apart second end (2414) and an inner wall (2416) and a radially spaced apart outer wall (2418). The blade housing includes a blade housing cover (2450) extending from the inner wall into the blade interior region. The blade housing cover includes a shield (2470) extending along the recessed upper portion of the rotary knife blade inner wall and having an inner surface (2472) adjacent and continuing the lower tissue-directing surface of the rotary knife blade inner wall.

24 Claims, 27 Drawing Sheets

(58) Field of Classification Search
CPC .... A01D 34/16; A01D 34/90; A01D 34/4161; A01D 34/4163; A22B 5/165; B26B 25/002
USPC .......................... 30/276; 606/131, 132, 180
See application file for complete search history.

(56) References Cited

U.S. PATENT DOCUMENTS

| | | | |
|---|---|---|---|
| 3,461,557 A * | 8/1969 | Behring | 30/276 |
| 3,688,403 A * | 9/1972 | Bettcher | 30/276 |
| 4,142,291 A * | 3/1979 | Bettcher | 30/276 |
| 4,166,317 A | 9/1979 | Bettcher | |
| 4,170,063 A | 10/1979 | Bettcher | |
| 4,198,750 A | 4/1980 | Bettcher | |
| 4,236,531 A | 12/1980 | McCullough | |
| 4,363,170 A | 12/1982 | McCullough | |
| 4,439,924 A * | 4/1984 | Bettcher | 30/276 |
| 4,492,027 A | 1/1985 | Bettcher | |
| 4,494,311 A | 1/1985 | McCullough | |
| 4,516,323 A | 5/1985 | Bettcher | |
| 4,575,937 A | 3/1986 | McCullough | |
| 4,575,938 A | 3/1986 | McCullough | |
| 4,590,676 A | 5/1986 | Bettcher | |
| 4,637,140 A * | 1/1987 | Bettcher | 30/276 |
| 4,854,046 A | 8/1989 | Decker et al. | |
| 4,858,321 A * | 8/1989 | McCullough | 30/276 |
| 5,230,154 A | 7/1993 | Decker et al. | |
| 5,522,142 A * | 6/1996 | Whited | 30/276 |
| 5,529,532 A | 6/1996 | Deerosiers | |
| 5,632,090 A | 5/1997 | Smith | |
| 5,664,332 A * | 9/1997 | Whited et al. | 30/276 |
| 5,692,307 A | 12/1997 | Whited et al. | |
| 5,761,817 A * | 6/1998 | Whited et al. | 30/276 |
| 5,940,972 A | 8/1999 | Baris et al. | |
| 6,604,288 B2 | 8/2003 | Whited et al. | |
| 6,615,494 B2 | 9/2003 | Long et al. | |
| 6,665,943 B1 | 12/2003 | Sloane et al. | |
| 6,694,649 B2 | 2/2004 | Whited et al. | |
| 6,751,872 B1 * | 6/2004 | Whited et al. | 30/276 |
| 6,769,184 B1 | 8/2004 | Whited | |
| 6,857,191 B2 | 2/2005 | Whited | |
| 6,880,249 B2 * | 4/2005 | Long et al. | 30/276 |
| 6,978,548 B2 | 12/2005 | Whited et al. | |
| 8,037,611 B2 | 10/2011 | Levsen | |
| 8,448,340 B2 | 5/2013 | Whited | |
| 8,661,692 B2 | 3/2014 | Whited et al. | |
| 8,739,416 B2 | 6/2014 | Mascari et al. | |
| 8,752,299 B2 | 6/2014 | Rosu et al. | |
| 8,756,819 B2 | 6/2014 | Whited et al. | |
| 8,806,761 B2 | 8/2014 | Whited et al. | |
| 9,186,171 B2 | 11/2015 | Esarey et al. | |
| 9,592,076 B2 | 3/2017 | Esarey et al. | |
| 2002/0096027 A1 | 7/2002 | Whited et al. | |
| 2003/0070301 A1 | 4/2003 | Herrmann et al. | |
| 2003/0084576 A1* | 5/2003 | Whited et al. | 30/276 |
| 2003/0131482 A1* | 7/2003 | Long et al. | 30/276 |
| 2003/0196333 A1 | 10/2003 | Whited | |
| 2004/0187316 A1 | 9/2004 | Whited et al. | |
| 2005/0126015 A1* | 6/2005 | Whited | 30/276 |
| 2005/0178009 A1 | 8/2005 | Whited | |
| 2005/0211067 A1 | 9/2005 | Bee, Jr. et al. | |
| 2005/0217119 A1 | 10/2005 | Rapp | |
| 2006/0037200 A1 | 2/2006 | Rosu et al. | |
| 2006/0137193 A1 | 6/2006 | Whited | |
| 2007/0283573 A1 | 12/2007 | Levsen | |
| 2007/0283574 A1 | 12/2007 | Levsen | |
| 2008/0098605 A1 | 5/2008 | Whited et al. | |
| 2010/0101097 A1 | 4/2010 | Thien | |
| 2010/0247220 A1 | 9/2010 | Maekawa | |
| 2011/0185580 A1 | 8/2011 | Whited | |
| 2011/0247220 A1 | 10/2011 | Whited et al. | |
| 2013/0025134 A1 | 1/2013 | Mascari et al. | |
| 2013/0025139 A1 | 1/2013 | Whited et al. | |
| 2013/0174424 A1 | 7/2013 | Whited et al. | |

OTHER PUBLICATIONS

International Search Report dated Dec. 12, 2013 and Written Opinion of the International Searching Authority dated Dec. 12, 2013 for PCT International Application No. PCT/US2013/058142, filed Sep. 5, 2013. PCT International Application No. PCT/US2013/058142 corresponds to and claims priority from the present application. (9 pages)(Exhibit B).

Oct. 3, 2011 Decision and Opinion of the United States Court of Appeals for the Federal Circuit (Appeal No. 2011-1038,-1046) regarding the case styled *Bettcher Industries, Inc.* v. *Burial USA, Inc. and Bunzl Processor Distribution, LLC*, Case No. 3:08 CV 2423, U.S. District Court for the Northern District of Ohio, Judge Zouhary. The Decision and Opinion relates to U.S. Pat. No. 7,00,325, owned by the assignee of the present application. (47 pages) (Exhibit C).

Catalog entitled "Ball Bearing Cages", Publication No. WLK 100 E, Publication Date—Sep. 2004, Published by International Customized Bearings. (34 pages) (Exhibit D).

Operators Manual for Integra Model C Air Dermatome Manufactured by Integra LifeSciences Corporation, Copyright 2009, Cincinnati, OH (82 pages) (Exhibit E).

Instruction Manual for Zimmer™ Air Dermatome, Manufactured by Zimmer Surgical, Inc., Dover, OH, Copyright 1992 (127 pages) (Exhibit F).

Operators Manual, Integra TM, Model SB Dermatome, Manufactured by Integra LifeSciences Corporation, Plainsboro, New Jersey, Copyright 2005 (6 pages) (Exhibit G).

Informational Brochure for Humeca Dermatome Blades, Manufactured by Humeca BV, Enschede, The Netherlands, publication date Oct. 2008 (1 page) (Exhibit H).

Image of Super Gyros Knife-Metal, manufactured by Optimal Automatics, Inc., Chicago, IL. Advertisement [online]. Retrieved from the Internet: URL:http://www.autodoner.com/autodoner/products/gyro-knife/super-gyros-knife-metal.aspx. The Super Gyros Knife depicted in the Internet printout is prior art to the present application. (3 pages) (Exhibit I).

14 Photographs of Super Gyros Knife, Model P, Manufactured by Optimal Automatics, Inc., Chicago, IL. The Super Gyros Knife depicted in the 6 photos is prior art to the present application (6 pages) (Exhibit J).

3 Photographs of Power Operated Gyros Knife, Manufacturer, Unknown. The Power Operated Gyros Knife depicted in the 3 photographs is prior art to present application (3 pages) (Exhibit K).

Image of Super Gyros Knife-Plastic, manufactured by Optimal Automatics, Inc., Chicago, IL. Advertisement [online]. Retrieved from the Internet: URL:http://www.autodoner.com/autodoner/products/gyro-knife/super-gyros-knife-plastic.aspx. The Super Gyros Knife depicted in the Internet printout is prior art to the present application. (4 pages) (Exhibit L).

Extended European Search Report dated Apr. 21, 2016 for European Patent Application No. 13834662.2, filed Mar. 17, 2015. European Patent Application No. 13834662.2 is a regional phase application of PCT International Application No. PCT/US2013/058142, International Filing Date Sep. 5, 2013, PCT International Application No. PCT/US2013/058142 corresponds to and claims priority from the present application, (8 pages).

Australian Examination Report No. 1 dated Nov. 30, 2016 for Australian Patent Application No. 2013312731, filed Feb. 27, 2016. Australian Patent Application No. 2013312731 is a national phase application of PCT International Application No. PCT/US2013/058142, International Filing Date Sep. 5, 2013. PCT International Application No. PCT/US2013/058142 corresponds to and claims priority from the present application. (3 pages).

* cited by examiner

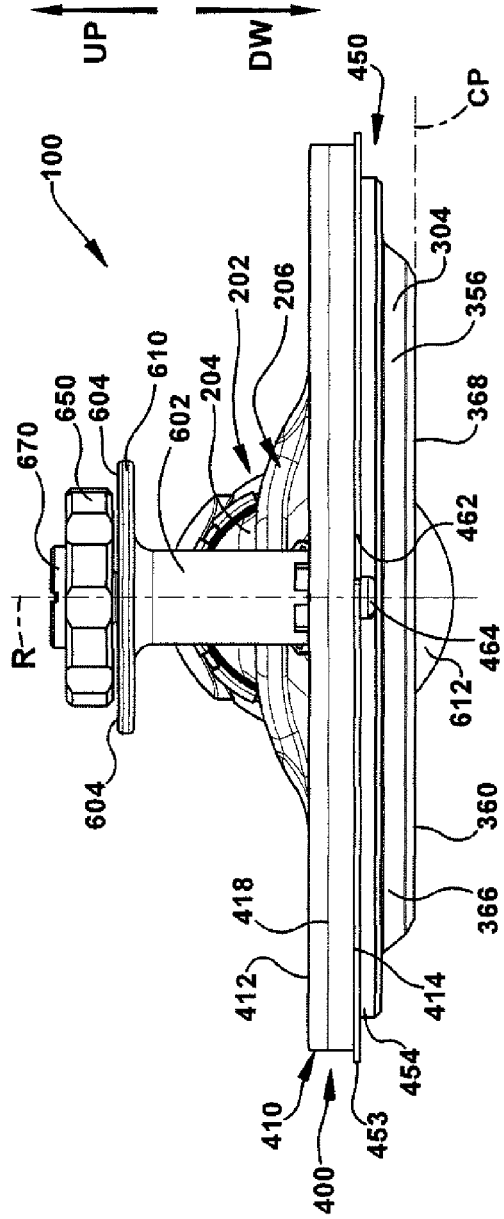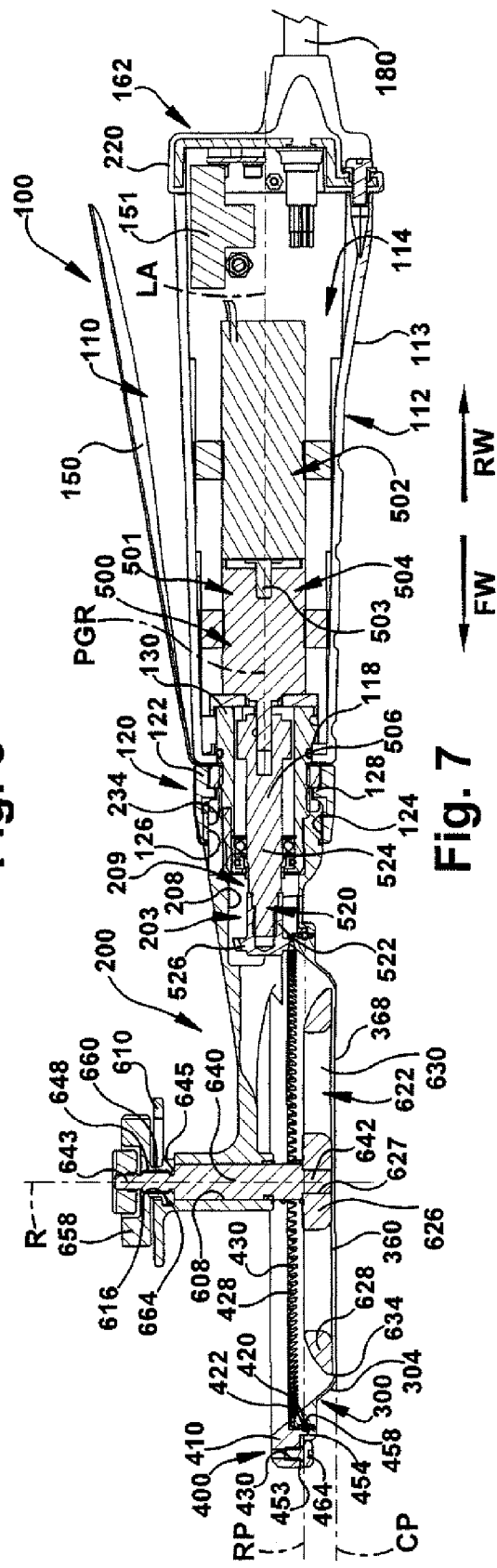

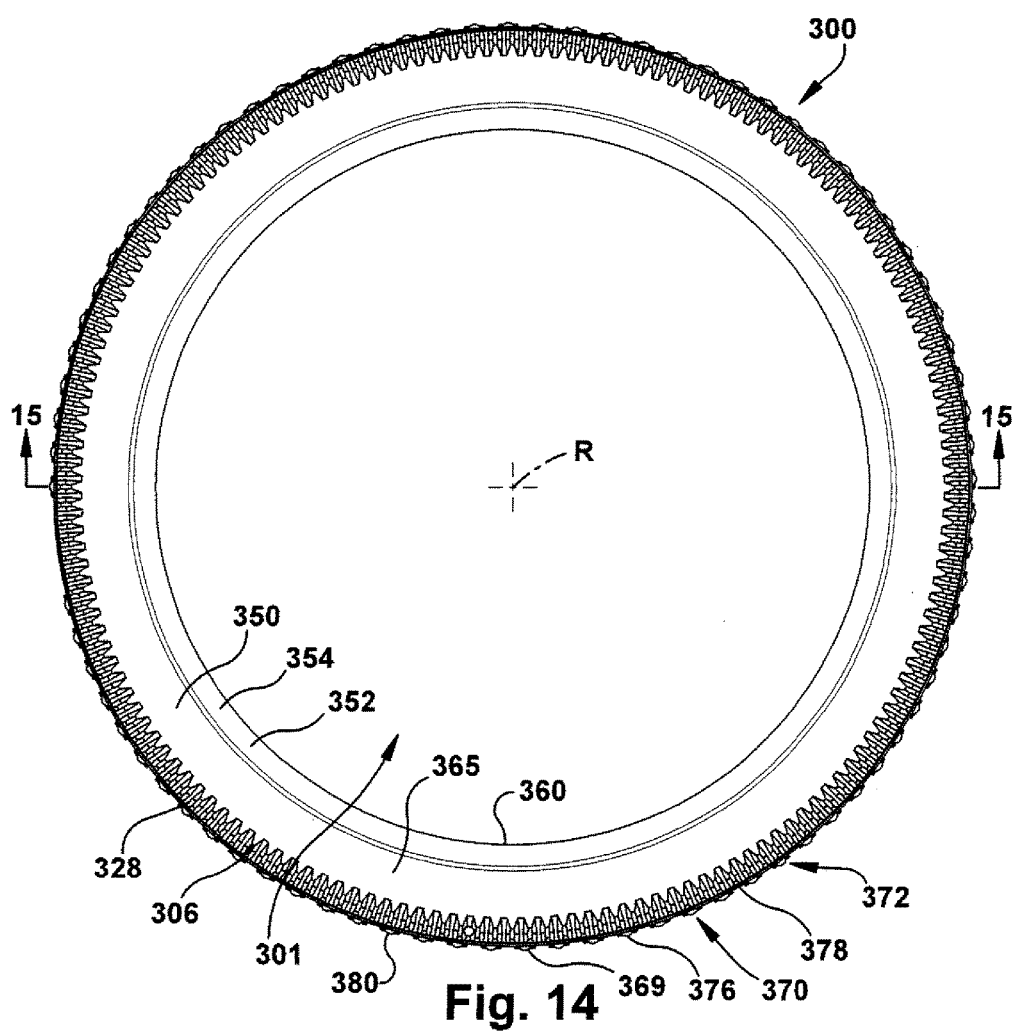
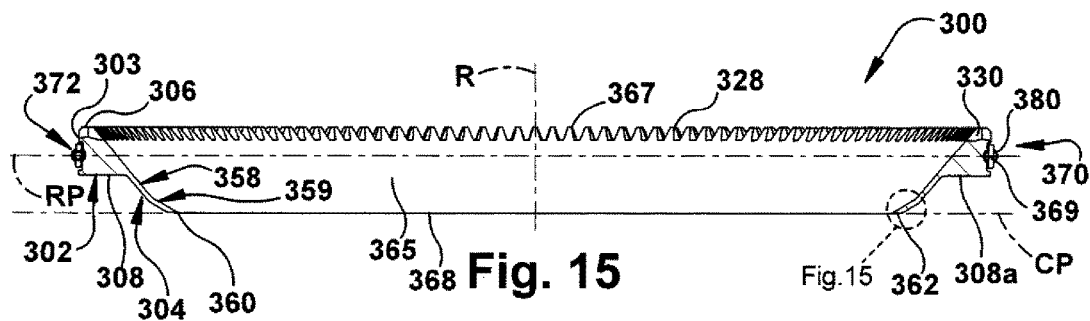

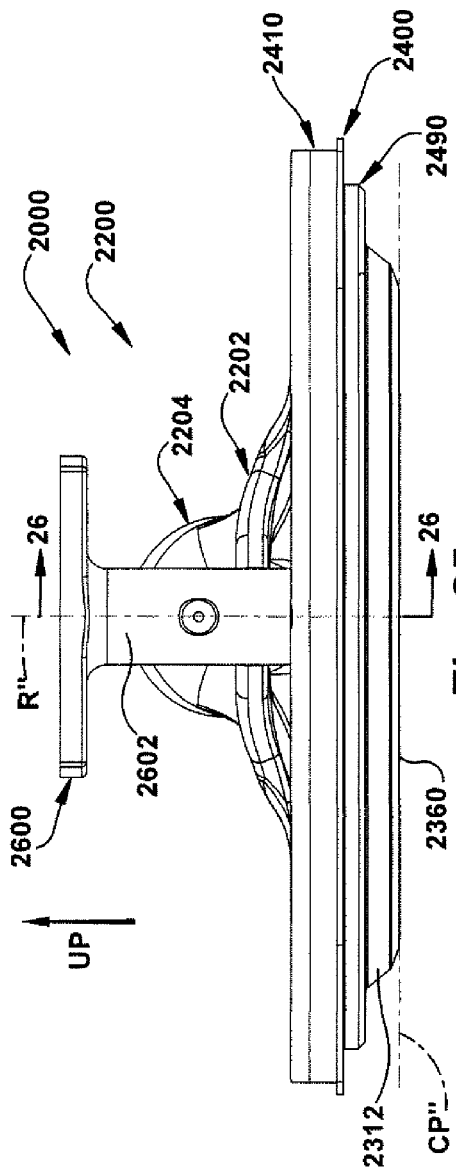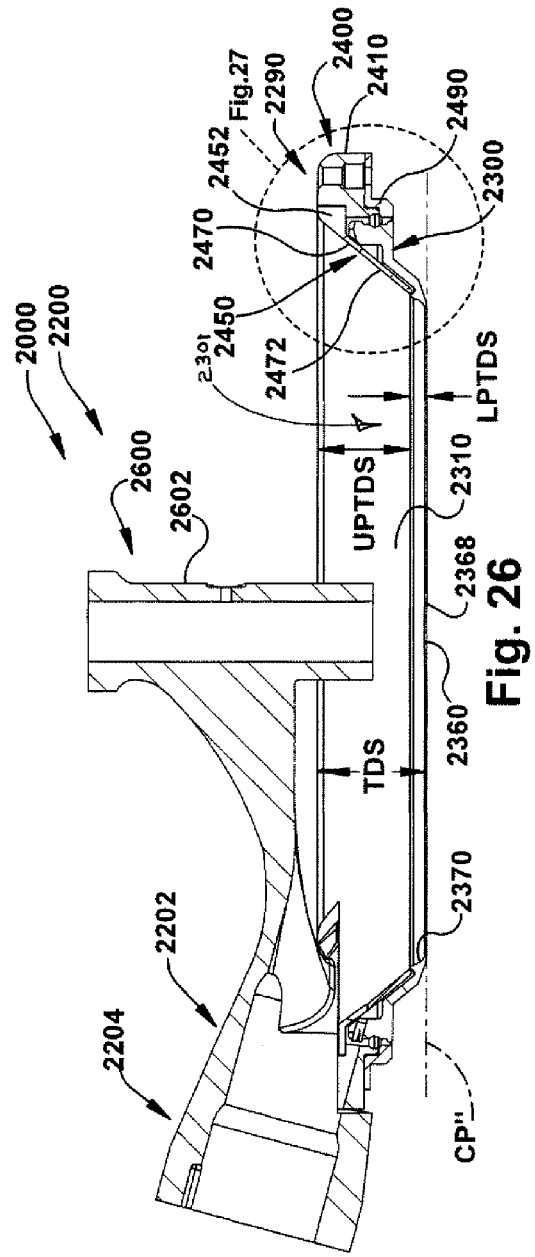
Fig. 25
Fig. 26

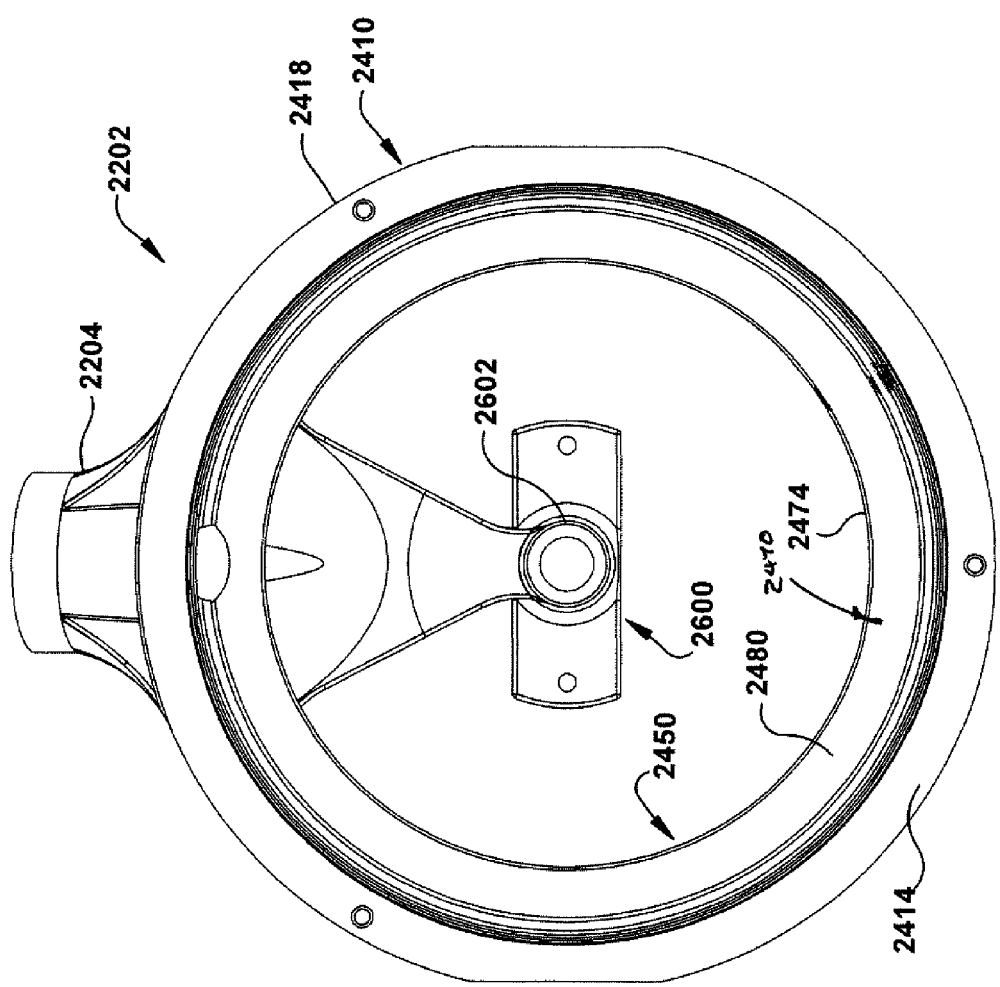

POWER OPERATED DERMATOME WITH SHIELDED ROTARY KNIFE BLADE

CROSS-REFERENCE TO RELATED APPLICATION

The present application is a continuation-in-part application of co-pending U.S. application Ser. No. 13/606,836, filed Sep. 7, 2012 and entitled POWER OPERATED DERMATOME WITH ROTARY KNIFE BLADE. The present application claims priority from above-identified application Ser. No. 13/606,836, which is incorporated herein in its entirety by reference, for all purposes.

TECHNICAL FIELD

The present disclosure relates to a power operated dermatome including a rotary knife blade and a blade housing assembly supporting the rotary knife blade for rotation about an axis of rotation, the rotary knife blade including an inner wall defining an interior region of the rotary knife blade and having a cutting edge at one end of the rotary knife blade defining a cutting plane orthogonal to the axis of rotation of the rotary knife blade, the blade housing assembly including a blade housing having a tissue-directing blade housing shield overlying an upper portion of the inner wall of the rotary knife blade.

BACKGROUND

Dermatomes are hand-held surgical instruments used by a physician or medical professional (hereinafter operator) for cutting thin layers or sections of skin tissue. Dermatomes are used in hospitals and other medical facilities for excising or removal of skin tissue from patients in connection with various medical procedures including split-thickness and full-thickness skin grafting, skin debriding (e.g., removal of burned skin tissue), tumor/lesion removal, and breast reduction, among other procedures. Dermatomes are also used in to remove skin tissue from deceased human or animal donors for skin grafting purposes.

Prior dermatomes included both manual operated and power operated dermatomes. Manual dermatomes typically included a fixed blade and a handle projecting from the blade. Manual dermatomes were often found tedious to use and prone to operator fatigue, especially when large sections of skin tissue needed to be removed, requiring multiple sections of skin tissue to be removed. For example, a deceased human donor may provide from 6-9 square feet of recoverable skin tissue.

It is generally desired that an excised skin section be of uniform or consistent thickness along the longitudinal extent of the skin section and across the width of the skin section. The thickness of an excised skin section is dependent on the depth of cut of the dermatome cutting blade. Use of manual dermatomes often resulted in excised skin sections of varying thickness and having irregular edges. The uniformity of the depth of cut was largely dependent on the skill of the operator. While limited numbers of manual dermatomes continue to be used, power operated dermatomes are favored in procedures where large sections of skin tissue need to be removed in an efficient manner and/or operator fatigue is an issue.

Prior power operated dermatomes typically included a reciprocating cutting blade disposed at a front or leading edge of the dermatome with a guard or depth gauge to allow the operator to set a depth of cut of the dermatome to remove a desired thickness of skin tissue. The blade was typically disposed orthogonally to a rearward extending handle or hand piece of the dermatome. Because the cutting direction of the blade of prior power operated dermatomes was forward facing, such dermatome configurations required the operator to move the dermatome in a direction generally away from the operator's body to excise or cut a section of skin tissue. This direction of movement of the operator's hand and the dermatome away from the operator's body is less natural and less precise that a direction of movement of the operator's hand and dermatome toward the operator. Moreover, in moving the dermatome away from the operator's body, the position of the dermatome tends to block the area of the skin tissue being excised from the view of the operator. This is especially problematic where the tissue to be removed is adjacent to, for example, a raised or bony prominence of the body that must be carefully navigated around with the cutting edge of the dermatome cutting blade.

Additionally, with prior power operated dermatomes, in order to cut a skin tissue section with a desired, consistent depth of cut, the angle of cut, the speed of the dermatome along the skin, and the pressure applied to the dermatome had to be carefully controlled by the operator. The angle of cut of the dermatome refers to an acute angle between the dermatome cutting blade and the skin tissue being removed or excised. If the angle of cut of the dermatome is too shallow, the desired depth of cut will not be achieved. If the angle of cut of the dermatome is too steep, gouging or trenching of the excised skin tissue will occur. Further, if the angle of cut is changed as the power operated dermatome is moved along the skin tissue, the depth of cut will vary along a longitudinal extent of the excised section of skin tissue.

The speed or rate of forward movement of prior power operated dermatomes also had to be carefully controlled by the operator. If the speed of the dermatome was too fast or too slow, the depth of cut of the excised skin section may be greater or less than the desired depth of cut as set by the operator using the dermatome depth gauge.

The operator using a typical prior power operated dermatome also was required to apply considerable pressure to the dermatome to insure that the entire extent or length of the cutting edge of the reciprocating blade remained in contact with the skin tissue. The pressure applied by the operator to the dermatome needed to remain constant. If the pressure applied by the operator to the dermatome was too high or too low during a cutting operation, the depth of cut could change and the excised skin section would have portions that were of greater or less depth than the desired depth of cut as set with the dermatome depth gauge. If the pressure applied by the operator to the dermatome was too low, the excised skin tissue may be too thin resulting in holes in the excised skin tissue and/or chattered edges.

Uniformity in the depth of cut of excised skin sections is especially important in split thickness skin grafts where it desired to remove only the outer epidermis and a portion of the dermis. Desired skin tissue thickness in a thin-type split-thickness skin graft is on the order of 0.127 to 0.304 mm. Thus, there is little margin for error where the desired skin thickness and depth of cut is very thin.

With prior dermatomes using a reciprocating blade, it was sometimes necessary for the operator to have an assistant provide counter-traction to flatten the skin surface in front of or behind the path of travel of the dermatome to allow the dermatome blade to make an initial cut. Adding an additional person to the procedure not only increases the cost of the procedure, but also increases the risk of infection and contamination due to the presence of another person in the operating or procedure room.

What is needed is a power operated dermatome wherein obtaining a desired, consistent thickness of an excised skin tissue section is less dependent on operator skill in maintaining a constant, desired angle of cut, speed and pressure on the dermatome. What is needed is a power operated dermatome that reduces operator fatigue when removing large sections of skin tissue. What is needed is a power operated dermatome that facilitates the removal of skin tissue in tight spaces and around boney prominences. What is needed is a power operated dermatome that facilitates improved control of the dermatome by the operator by moving the blade cutting edge along a path toward the operator, instead of moving the blade away from the operator. What is needed is a power operated dermatome that allows for improved visibility of the skin site being excised by the operator. What is needed is a power operated dermatome that facilitates removal of very thin layers of skin tissue and tangential excision of burn tissue. What is needed is a power operated dermatome that does not require an additional person involved in the procedure to provide counter-traction at the skin removal site to permit an initial cut to be made by the dermatome.

SUMMARY

In one aspect, the present disclosure relates to a head assembly for a power operated dermatome, the head assembly comprising: a frame body supporting a gear train, a blade housing assembly, an annular rotary knife blade supported for rotation about an axis of rotation by the blade housing assembly, the rotary knife blade including an inner wall defining an interior region of the rotary knife blade and having a cutting edge at one end of the rotary knife blade defining a cutting plane orthogonal to the axis of rotation of the rotary knife blade, and a depth gauge assembly including a depth gauge support and a depth gauge including a depth gauge plate supported by the depth gauge for axial movement along the axis of rotation of the rotary knife blade, the depth gauge plate extending into the interior region of the rotary knife blade and the depth gauge support attached to and extending from the frame body.

In another aspect, the present disclosure relates to a power operated dermatome comprising: an elongated handle assembly and a head assembly removably coupled to the handle assembly, the head assembly including a frame body supporting a gear train, a blade housing assembly, an annular rotary knife blade supported for rotation about an axis of rotation by the blade housing assembly, the rotary knife blade including an inner wall defining an interior region of the rotary knife blade and having a cutting edge at one end of the rotary knife blade defining a cutting plane orthogonal to the axis of rotation of the rotary knife blade, and a depth gauge assembly including a depth gauge support and a depth gauge including a depth gauge plate supported by the depth gauge for axial movement along the axis of rotation of the rotary knife blade, the depth gauge plate extending into the interior region of the rotary knife blade and the depth gauge support attached to and extending from the frame housing.

In another aspect, the present disclosure relates to a combination of an annular rotary knife blade and a blade housing assembly for a power operated dermatome, the combination comprising: the rotary knife blade supported for rotation about an axis of rotation by the blade housing assembly, the rotary knife blade including a first end and an axially spaced apart second end and an inner wall and a radially spaced apart outer wall, the second end defining a cutting edge, the inner wall defining an interior region of the rotary knife blade and including a lower material-directing surface adjacent the cutting edge and a radially recessed upper portion; and the blade housing assembly including a blade housing having a first end and an axially spaced apart second end and an inner wall and a radially spaced apart outer wall, the blade housing including a blade housing cover extending from inner wall into the interior region of the rotary knife blade, the blade housing cover including a shield extending along the recessed upper portion of the rotary knife blade inner wall and having an inner surface adjacent to and continuing the lower material-directing surface of the rotary knife blade inner wall.

In another aspect, the present disclosure relates to a combination of a rotary knife blade and a blade housing assembly for a power operated dermatome, the rotary knife blade supported for rotation about an axis of rotation by the blade housing assembly and the combination defining a tissue-directing surface for tissue cut by the rotary knife blade, the combination comprising: the rotary knife blade including an first end and an axially spaced apart second end and an inner wall and a radially spaced apart outer wall, the second end having a cutting edge defining a cutting plane substantially orthogonal to the axis of rotation, the inner wall defining an interior region of the rotary knife blade and including a tissue-directing surface adjacent the cutting edge and a radially recessed upper portion; and the blade housing assembly including a blade housing having a first end and an axially spaced apart second end and an inner wall and a radially spaced apart outer wall, the blade housing including a blade housing cover extending from inner wall into the interior region of the rotary knife blade, the blade housing cover including a shield extending along the recessed upper portion of the rotary knife blade inner wall and having a tissue-directing inner surface adjacent to and continuing the lower tissue-directing surface of the rotary knife blade inner wall, the tissue-directing surface of the rotary knife blade and the tissue-directing surface inner surface of the blade housing shield comprising the tissue-directing surface of the combination.

In another aspect, the present disclosure relates to a head assembly for a power operated dermatome, the head assembly comprising: a frame body supporting a gear train, a blade housing assembly, an annular rotary knife blade supported for rotation about an axis of rotation by the blade housing assembly, the rotary knife blade including the rotary knife blade including a first end and an axially spaced apart second end and an inner wall and a radially spaced apart outer wall, the second end defining a cutting edge, the inner wall defining an interior region of the rotary knife blade and including a lower material-directing surface adjacent the cutting edge and a radially recessed upper portion; and the blade housing assembly including a blade housing having a first end and an axially spaced apart second end and an inner wall and a radially spaced apart outer wall, the blade housing including a blade housing cover extending from inner wall into the interior region of the rotary knife blade, the blade housing cover including a shield extending along the recessed upper portion of the rotary knife blade inner wall and having an inner surface adjacent to and continuing the lower material-directing surface of the rotary knife blade inner wall

BRIEF DESCRIPTION OF THE DRAWINGS

The foregoing and other features and advantages of the present disclosure will become apparent to one skilled in the art to which the present disclosure relates upon consideration of the following description of the invention with reference to the accompanying drawings, wherein like reference numerals, unless otherwise described refer to like parts throughout the drawings and in which:

FIG. 6 is a schematic front elevation view of the power operated dermatome of FIG. 1;

FIG. 7 is a schematic longitudinal section view of the power operated dermatome of FIG. 1, as viewed along a longitudinal axis LA of the handle assembly of the dermatome;

FIG. 14 is a schematic front elevation view of an exemplary embodiment of the rotary knife blade of the power operated dermatome of FIG. 1;

FIG. 15 is a schematic section view of the rotary knife of FIG. 14, as seen from a plane indicated by the line 15-15 in FIG. 14;

FIG. 17 is a schematic section view of the power operated dermatome of FIG. 1, as manipulated to make an initial incision or cut in skin tissue for a thin type, split thickness skin graft wherein a depth of a layer of skin tissue being excised from a patient or donor graft site is on the order of 0.005 in. to 0.012 in.;

FIG. 18 is a schematic view, partially in perspective and partially in section, of the power operated dermatome of FIG. 1, as manipulated to cut or excise a thin type, split thickness skin graft wherein a depth of a layer of skin tissue being excised from a patient or donor graft site is on the order of 0.005 in. to 0.012 in.;

FIG. 19 is a schematic view, partially in perspective and partially in section, of the power operated dermatome of FIG. 1, as manipulated to terminate an incision in a thin type, split thickness skin graft wherein a depth of a layer of skin tissue being excised from a patent or donor graft site is on the order of 0.005 in. to 0.012 in.;

FIG. 20 is a schematic view, partially in perspective and partially in section, of the power operated dermatome of FIG. 1, as used in a full thickness skin graft wherein a depth of a layer of skin tissue being excised from a donor graft site is on the order of 0.030 in. to 0.043 in.;

FIG. 25 is a schematic front elevation view of a head assembly of a third exemplary embodiment of a hand held power operated dermatome of the present disclosure, the head assembly comprising a rotary knife blade and a blade housing assembly including a blade housing having a stationary tissue-directing shield overlying an upper portion of an inner wall of the rotary knife blade;

FIG. 26 is a schematic longitudinal section view of the head assembly of FIG. 25, as seen from a plane indicated by the line 26-26 in FIG. 25;

FIG. 31 is a schematic bottom plan view of the head assembly of FIG. 25 with a rotary knife blade and a blade lock ring of a blade housing assembly removed.

DETAILED DESCRIPTION

The present disclosure relates to a hand-held, power operated dermatome 100 for medical use in removing a layer of skin tissue SK (FIGS. 17-21) from a patient or donor in connection with various medical procedures including split-thickness and full-thickness skin grafting, skin debriding, e.g., removal of burned skin tissue, tumor/lesion removal, breast reduction, among other procedures, including removing a layer of skin tissue from a deceased human or animal donor for skin grafting/transplanting purposes. Advantageously, the dermatome 100 of the present disclosure includes an annular rotary knife blade 300 that is driven about a central axis of rotation R at a high rotational speed (on the order of 500-1,500 RPM) by a drive assembly 500 of the dermatome 100 and further includes a depth gauge assembly 600 to allow precise setting and adjustment of a depth of cut DOC of the dermatome 100.

Figure 18:
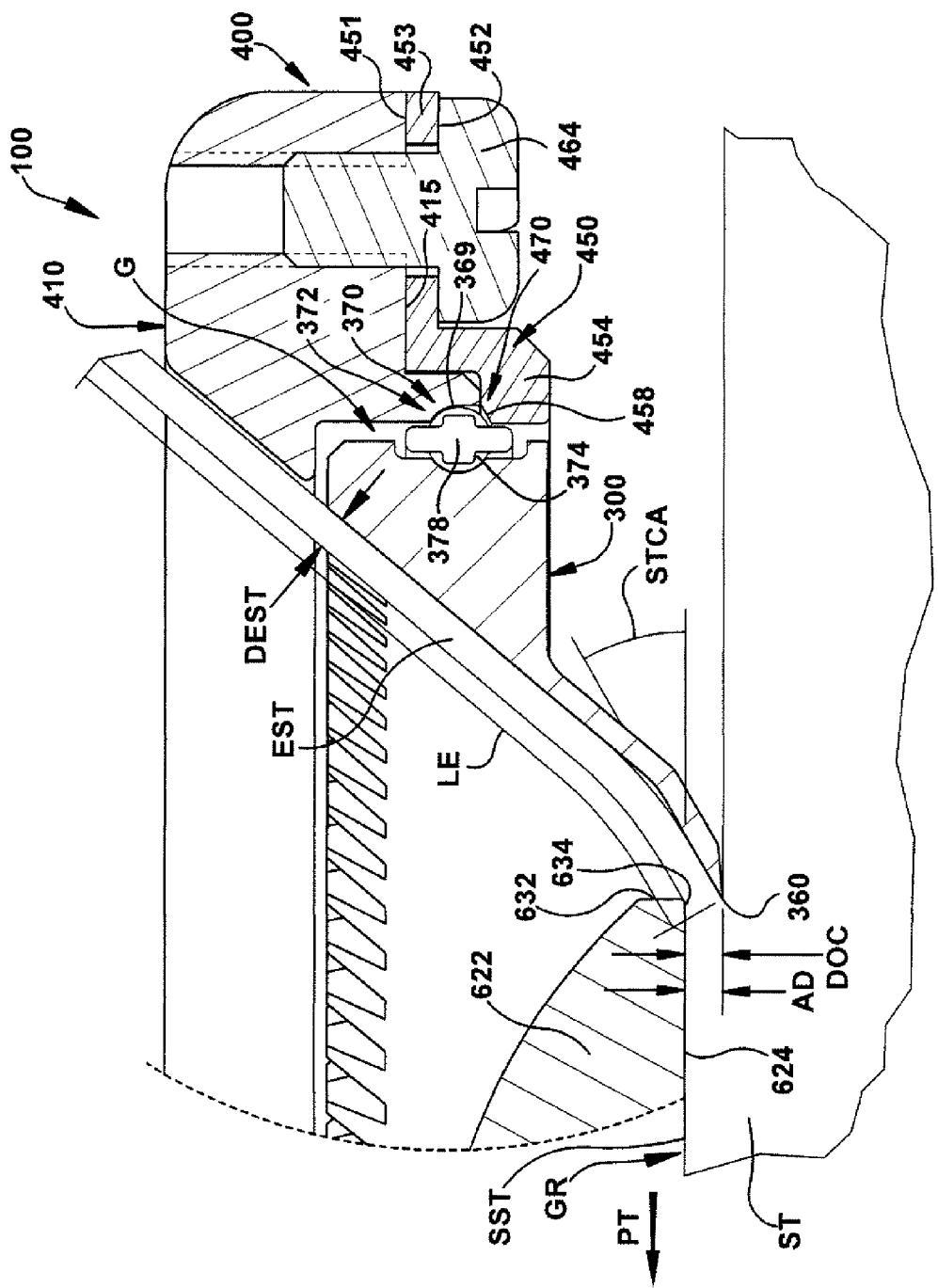
Figure 19:
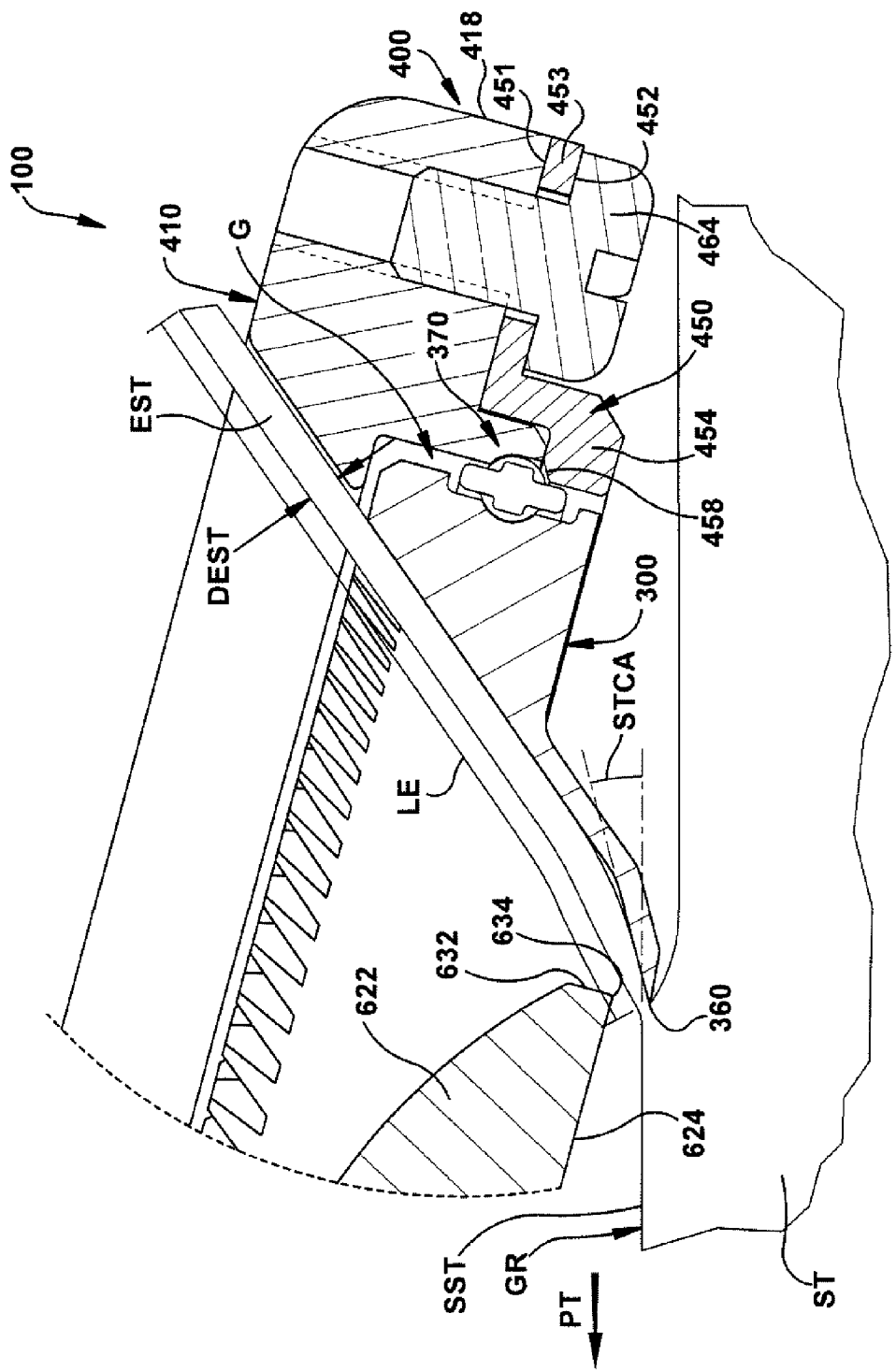
Figure 20:
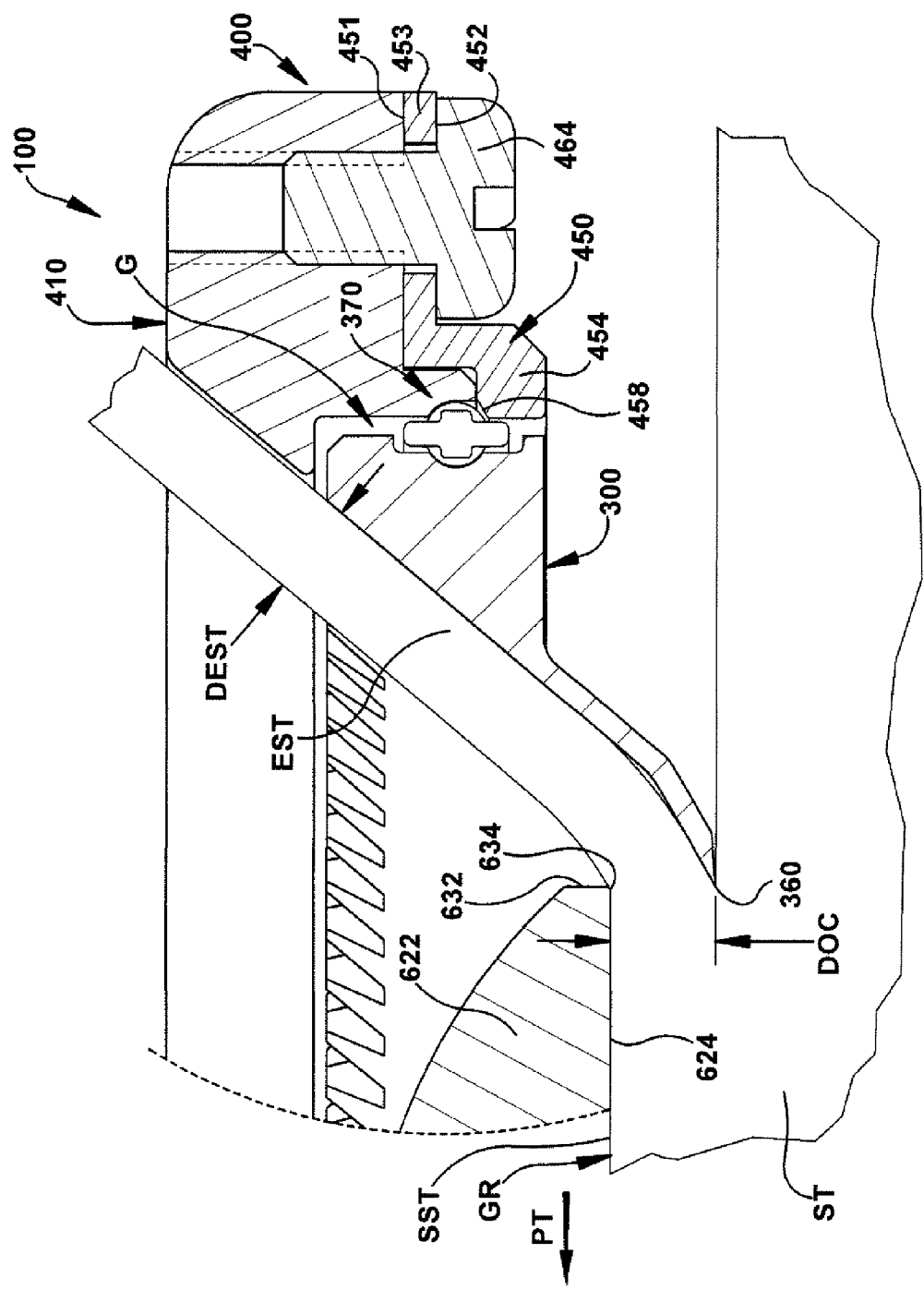

A cutting edge 360 of the rotary knife blade 300 cuts or excises an upper layer of skin tissue SK from a grafting region GR, resulting in an excised section or layer of skin tissue EST, as illustrated in FIGS. 18-20. In the dermatome 100 of the present disclosure, a cutting angle CA (FIGS. 7, 12, 13 and 16) of the blade section 304 adjacent the cutting edge 360 with respect to a cutting plane CP of the rotary knife blade 300 is relatively shallow. In one exemplary embodiment, the cutting angle CA is approximately 30° with respect to the cutting plane CP. The depth gauge assembly 600 of the dermatome 100 includes an axially adjustable depth gauge 620. The axially adjustable depth gauge 620 includes a depth gauge plate 622 and a depth gauge shaft 640 affixed to the depth gauge plate 622. The depth gauge 620 extends into a central opening 301 defined by the rotary knife blade 300.

An axial position of the depth gauge plate 622 with respect to the cutting edge 360 of the rotary knife blade 300 is determined by a rotation position of a depth adjustment knob 650 of the depth gauge assembly 600. The axial position of the gauge plate 622 of the depth gauge 620 with respect to the cutting edge 360 of the rotary knife blade 300 sets the depth of cut DOC of the dermatome 100. The depth of cut DOC of the dermatome 100 determines the depth or thickness of a section of skin tissue SK excised by the dermatome 100. The depth or thickness of an excised skin tissue section or layer is labeled as DEST in FIGS. 18-20. That is, the depth or thickness of an excised skin tissue section DEST of a patient or donor is determined by the depth of cut DOC of the dermatome 100, as precisely set by the operator of the dermatome 100 using the depth adjustment knob 650.

As compared to prior manual or power operated dermatomes, the high rotary speed of the rotary knife blade 300 of the dermatome 100 of the present disclosure, in combination with a shallow cutting angle CA of the knife blade 300 and configuration of the depth gauge assembly 600 and, specifically, the depth gauge plate 622, facilitate an operator's ability to cut or harvest an excised layer of skin tissue EST having a desired depth of cut of the excised tissue DEST that is more uniform and consistent along a longitudinal extend LE (FIGS. 18 and 19) of the excised skin tissue EST than what would be expected using a prior manual dermatome or a prior power operated dermatome. The dermatome 100 of the present disclosure advantageously provides for improved control and manipulation of the dermatome 100 by an operator, using one hand, as the dermatome 100 is moved along a path of travel PT to cut the skin tissue SK to produce the excised skin section EST. Moreover, the high rotary speed of the rotary knife blade 300 of the dermatome 100 reduces operator fatigue when removing large sections of skin tissue ST in a grafting region GR. The high rotary speed of the rotary knife blade 300 also facilitates making an initial incision (FIG. 17) in a layer of skin tissue SK at the cutting edge 360 of the rotary knife blade 300 without the need for applying counter traction to the skin tissue ST in the grafting region GR.

Advantageously, rotation of the depth adjustment knob 650 of the depth gauge assembly 600 quickly and precisely changes the axial position of the depth gauge plate 622 with respect to the cutting edge of the rotary knife blade 300, thereby allowing the operator to change the depth of cut DOC of the dermatome 100, as desired. The depth of cut DOC of the dermatome 100 directly determines the resulting excised skin tissue depth of cut DEST. By way of example and without limitation, the dermatome 100 of the present invention may be advantageously used for split thickness skin grafting (schematically depicted in FIGS. 17-19) and full thickness skin grafts (schematically depicted in FIG. 20). Approximate depth or thickness ranges for split thickness skin grafting may be categorized into three types of split thickness skin grafting: a) thin-type—skin tissue depth range 0.005 in.-0.012 in.; b) intermediate-type—depth range 0.012 in.-0.018 in.; and c) thick-type—depth range 0.018 in-0.030 in. The approximate depth or thickness range for full thickness skin grafting is 0.030 in.-0.043 in.

Figure 17:
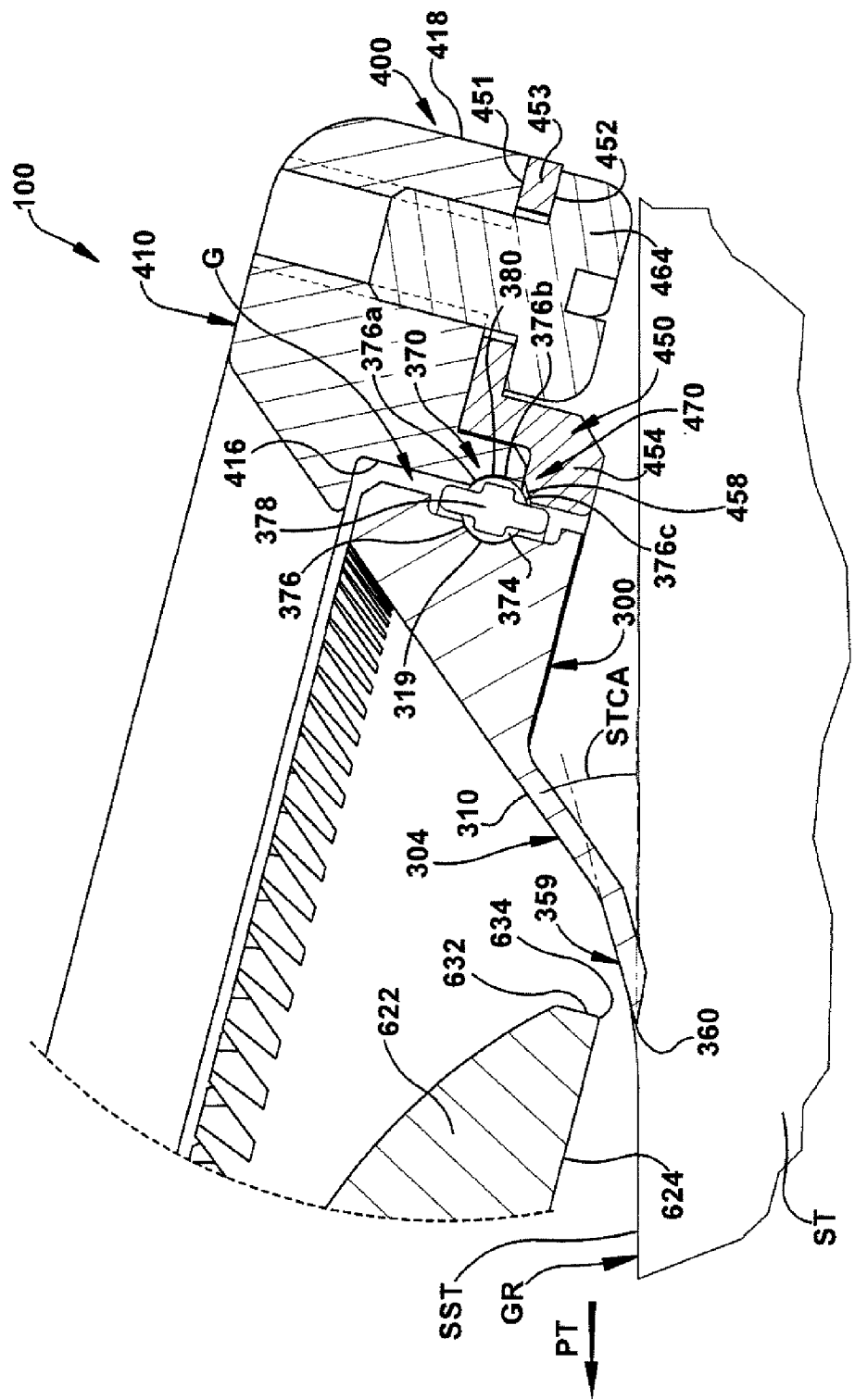

The dermatome 100 of the present disclosure provides for both rapid and precise adjustment of the dermatome depth of cut DOC and improved control and manipulation of the dermatome 100. These features enhance the ability of an operator to produce an excised skin tissue section EST having a desired depth of excised skin tissue DEST and having a consistent or uniform depth along the longitudinal extent LE of the excised skin tissue section EST, even when undertaking thin-type, split-thickness skin grafts wherein the desired depth or thickness of the excised skin tissue EST is in a range of approximately 0.005 in. to 0.012 in. in depth (FIGS. 17-19). Advantageously, the operator need only keep the cutting edge 360 of the dermatome 100 flush or flat against the skin tissue ST as the dermatome 100 is moved along its path of travel PT to excise a section of skin tissue EST. This makes the cutting procedure less dependent on operator skill level, as opposed to a cutting procedure where the operator was required to maintain a particular angle of the dermatome with respect to the skin tissue as the dermatome is moved along its path of travel or where the operator was required to change the angle of the dermatome with respect to the skin tissue as the dermatome is moved along its path of travel. The characteristics of the dermatome 100 of the present disclosure allow an operator to cut excised skin tissue sections EST of desired depth and substantially uniform depth from a patient/donor grafting region GR with less dependence on operator skill and more dependence on the attributes and characteristics of the dermatome 100.

Figure 5:
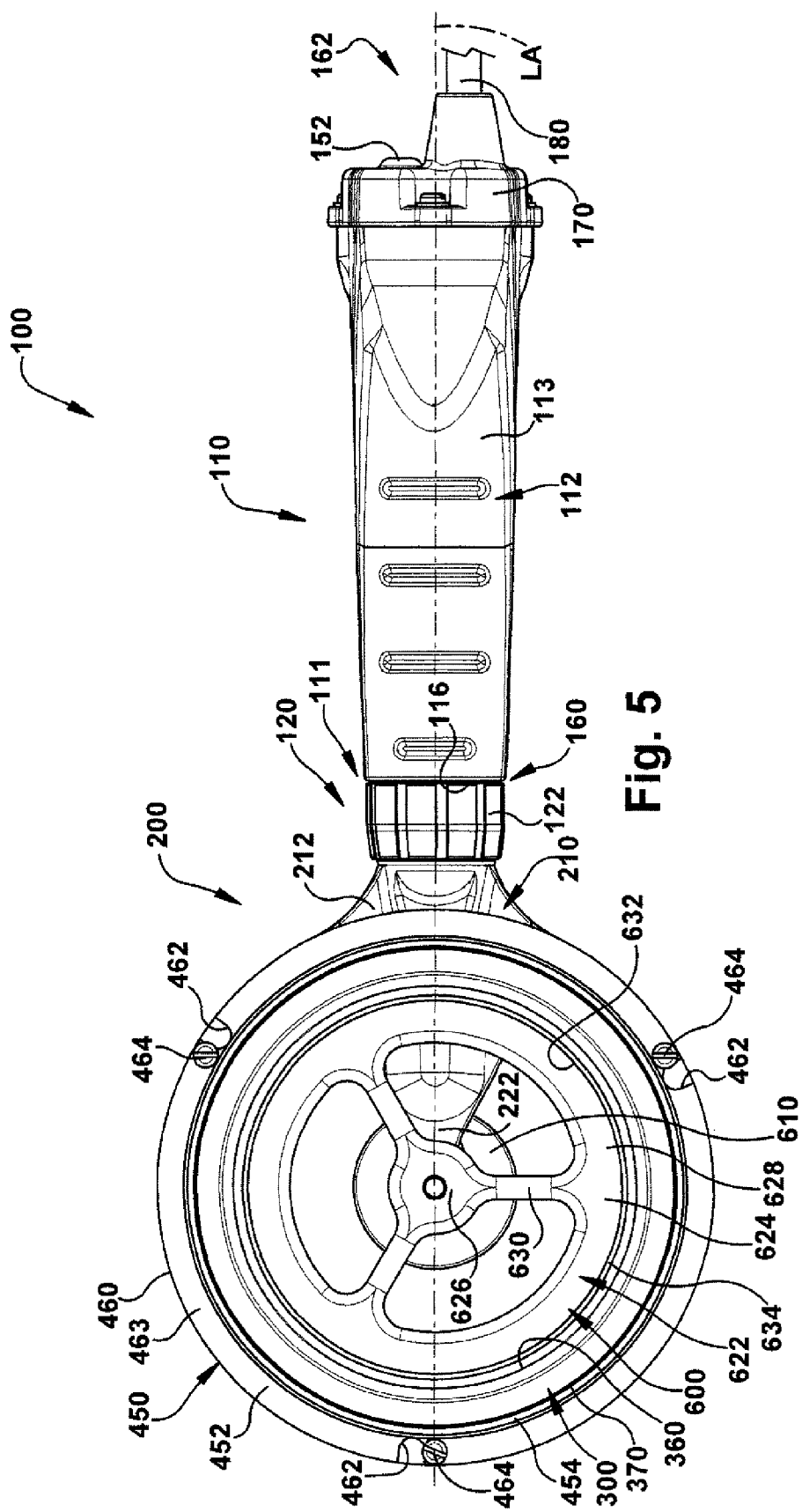
FIG. 5 is a schematic bottom plan view of the power operated dermatome of FIG. 1.
Figure 8:
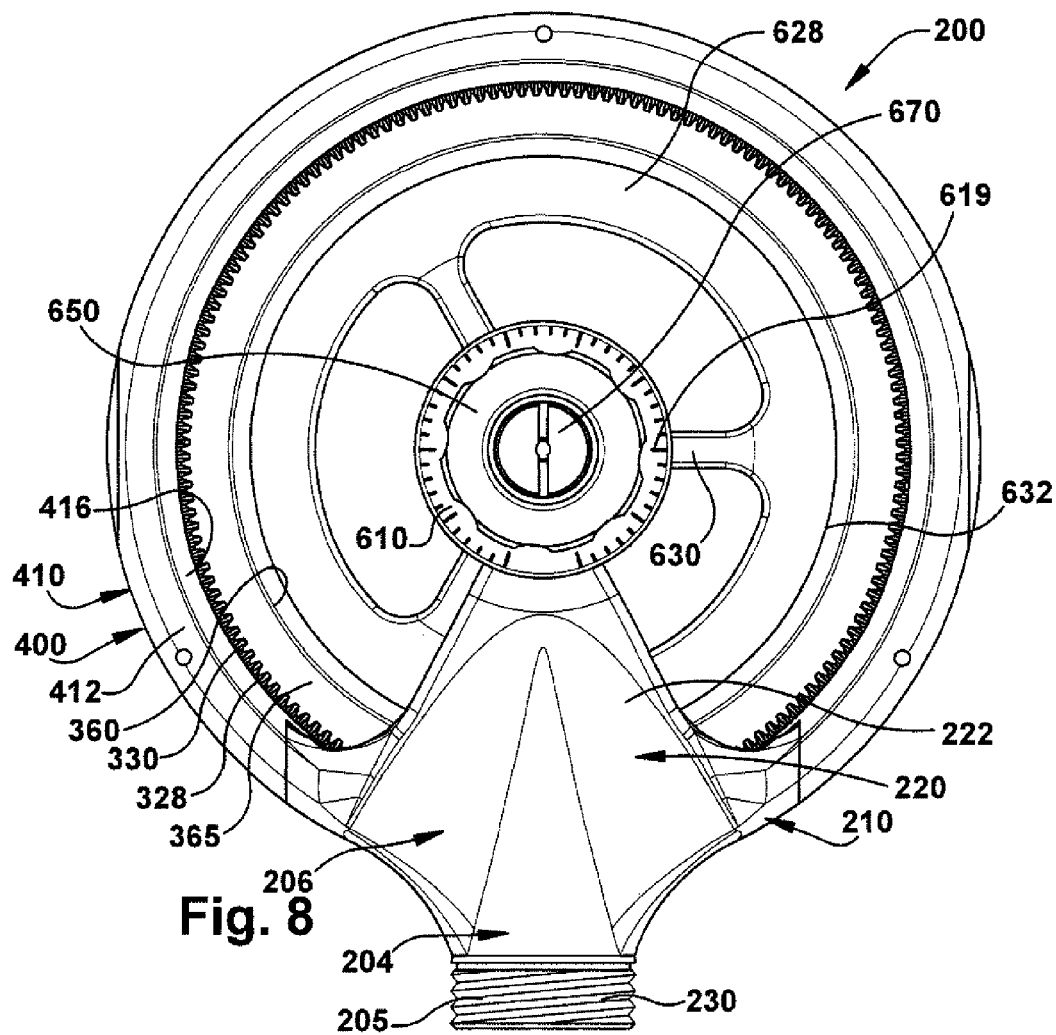
FIG. 8 is a schematic top plan view of the head assembly of the power operated dermatome of FIG. 1, with a gear train of the head assembly removed for clarity.
Figure 9:
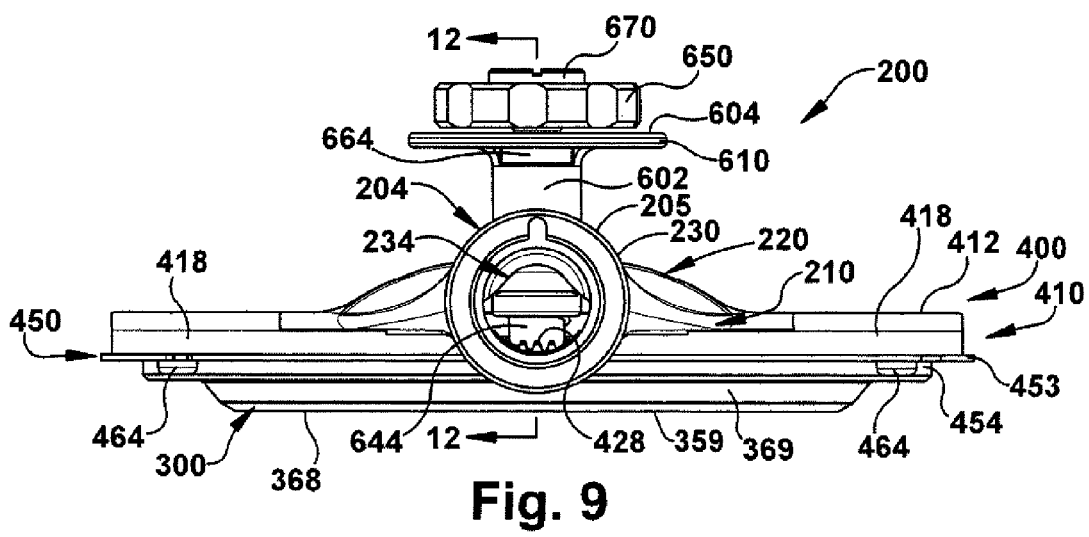
FIG. 9 is a schematic rear elevation view of the head assembly of FIG. 8.

Moreover, as can be seen in FIG. 5, because the cutting edge 360 of the rotary knife blade 300 of the dermatome 100 extends around the entire 360° circumference of the rotary knife blade 300, a cutting region of the dermatome 100 likewise extends 360° around the cutting edge 360. Thus, unlike prior manual or power operated dermatomes having a straight cutting blade and, therefore, were generally limited to a single cutting direction, the dermatome 100 of the present disclosure may advantageously used in any desired cutting direction—toward the operator, away from the operator, parallel to the operator, and any direction therebetween. Thus, the dermatome 100 of the present disclosure can be moved in various directions, as desired by the operator, to cut skin tissue SK from a grafting region GR, including a natural movement of sweeping the operator's hand and arm in a generally arcuate path inwardly toward the operator's body, thereby cutting the skin tissue section ST as the dermatome 100 along a generally arcuate path toward the operator's body. Advantageously, such a "toward the operator" cutting direction of the dermatome 100 facilitates a clear view of the grafting region GR by the operator. Further, advantageously, the range of cutting directions afforded by the dermatome 100 of the present disclosure facilitates maneuvering of the dermatome 100 around tight spaces and/or boney prominences in the grafting region GR.

First Exemplary Embodiment-Power Operated Dermatome 100

Figure 16:
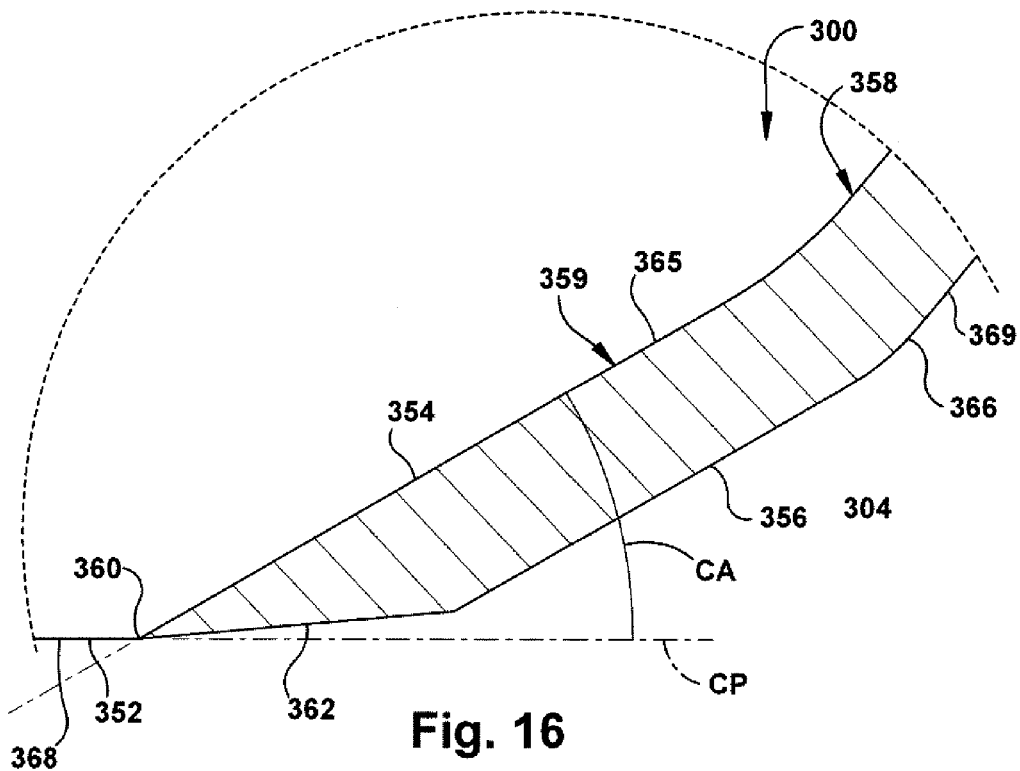
FIG. 16 is a schematic enlarged section view of a cutting edge portion of the rotary knife blade shown FIG. 15 that is within a dashed circle labeled FIG. 16 in FIG. 15.

A first exemplary embodiment of a hand-held, power operated dermatome of the present disclosure is schematically shown at 100 in FIGS. 1-7. The power operated dermatome 100 includes an elongated handle assembly 110 and a head assembly 200 extending from a forward or distal end 160 of the handle assembly 110. An attachment assembly 120 releasably affixes the head assembly 200 to the handle assembly 110. As is best seen in FIGS. 8-13, the head assembly 200 includes a frame body or frame housing 202, the rotary knife blade 300, an annular blade housing assembly 400 which rotatably supports the rotary knife blade 300 for rotation about the central axis of rotation R and the depth gauge assembly 600. The blade housing assembly 400 includes an annular blade housing 410 and a blade lock ring 450 which is releasably affixed to the blade housing 410 to trap and secure the rotary knife blade 300 for rotation with respect to the blade housing assembly 400. As is best seen in FIGS. 14-16, the rotary knife blade 300 includes a body section 302, a blade section 304 and a continuous rolling bearing structure 370 defining a portion of an outer peripheral surface 369 (FIG. 13) of the rotary knife blade 300. As can best be seen in FIG. 17, the continuous rolling bearing structure 370 is permanently affixed to a concave bearing surface 319 of the rotary knife blade body section 302 and, in turn, defines a convex bearing surface 380 of the rotary knife blade 300.

As can be seen schematically in FIG. 7, the rotary knife blade 300 is rotated with respect to the blade housing assembly 400 about the central axis of rotation R by a drive assembly 500 which includes a drive motor assembly 501 and a gear train 520. In one exemplary embodiment, the drive motor assembly 501 is supported by the handle assembly 110, while the gear train 520 is supported by a gearbox housing 203 of the frame body 202 of the head assembly 200. The depth gauge assembly 600 is also supported by the frame body 202 and includes a depth gauge support 602. The depth gauge support 602, which extends from the frame body 202, in turn, supports the depth gauge 620 including the depth gauge plate 622 and depth gauge shaft 640. The depth gauge 620 extends into the central interior region 301 of the rotary knife blade 300.

Handle Assembly 110 & Attachment Assembly 120

As can best be seen in FIGS. 1-5 and 7, the handle assembly 110 extends between the forward or distal end 160 and a rearward or proximal end 162 and includes an elongated handle 112 and a proximal or rear handle cover 170. The handle assembly 110 establishes and extends along a longitudinal axis LA. The longitudinal axis LA of the handle assembly 110 establishes a longitudinal axis of the dermatome 100. In one exemplary embodiment, the handle assembly longitudinal axis LA is substantially orthogonal to and intersects the central axis of rotation R of the rotary knife blade 300. An outer surface 113 of the handle 112 is contoured for easy gripping by the operator. The handle 112 includes a generally cylindrical, longitudinal throughbore 114 which supports the drive motor assembly 501 of the drive assembly 500. A forward or front end 116 of the handle 112 includes a radially inwardly stepped portion 118 that serves as an attachment point for the attachment assembly 120.

In one exemplary embodiment, the drive motor assembly 501 is actuated by a combination of an actuation lever 150 which is pivotally mounted with respect to the handle 112, a lever sensing switch 151, and an actuation switch 152. When the actuation lever 150 is pivoted to an "on" position, generally parallel to the outer surface 113 of the handle 112, a lever sensing switch 151 disposed within the handle throughbore is tripped. An actuation switch 152 is located on the cover 170 at the proximal end 162 of the handle assembly 110. When the actuation lever 150 is pivoted to the "on" position and the actuation switch 152 is pressed within five seconds of the tripping of the lever sensing switch 151, the drive assembly 500 is actuated to rotate the rotary knife blade 300. If the actuation switch 152 is not pressed within five seconds of the tripping of the lever sensing switch 151, the actuation lever 150 must be released and again pivoted to the "on" position. Alternately, the drive motor assembly 501 may be actuated by a foot pedal valve positioned at the feet of the operator affixed to the handle assembly 110 or a toggle or rocker switch mounted on the handle assembly 110.

The handle assembly 110 extends orthogonally in a rearward direction RW (FIG. 7) away from the head assembly 200 along the handle axis longitudinal axis LA. The longitudinal axis LA is substantially orthogonal to the blade central axis of rotation R and parallel to the cutting plane CP of the rotary knife blade 300. This configuration allows the operator of the dermatome 100 to wield and manipulate the dermatome 100 effectively using one hand. The rear handle cover 170 of the handle assembly 110 overlies a proximal end of the handle 112 and is coupled to an air line or air hose 180 which provides a source of high pressure air to provide motive power to the drive motor assembly 501.

The attachment assembly 120 includes a coupling collar 122, a retainer 128 and an inner sleeve 130 that attaches to the inwardly stepped portion 118 at the front end 116 of the handle 112. The coupling collar 122 includes an inner surface 124 having a threaded portion 126. As can best be seen in FIG. 7, the coupling collar 122 is rotatably secured to the handle 112 by the retainer 128 and the inner sleeve 130. In turn, the coupling collar 122 threads onto a threaded outer surface 230 of the frame body 202 to releasably secure the head assembly 200 to the forward end 160 of the handle assembly 110. Advantageously, the attachment assembly 120 allows for easy coupling and decoupling of the head assembly 200 from the handle assembly 110 to facilitate disassembly and sterilization of components of the head assembly 200 upon completion of a skin grafting or other medical procedure performed with the dermatome 100.

As used herein, axial, upper and lower shall mean movement or a dimension in a direction generally along or parallel to an extent of the central axis of rotation R. Forward or distal shall mean in a direction generally along a direction labeled FW in FIG. 7, the forward direction FW being generally parallel to or along the longitudinal axis LA. Rearward or proximal shall mean a direction generally along a direction labeled RW (opposite of the forward direction FW) in FIG. 7.

Drive Assembly 500

As best seen in FIG. 7, the drive assembly 500 includes the drive motor assembly 501 and the gear train 520. The present disclosure contemplates at least three different drive motor assemblies, an air motor embodiment (schematically shown in FIG. 7) and, alternatively, an electric motor disposed in the handle assembly (not shown), and a flexible drive shaft embodiment (not shown) to provide motive power to rotate the rotary knife blade 300 within the blade housing assembly 400. In one exemplary embodiment, the drive motor assembly 501 includes a vane-type air or pneumatic motor 502 and a planetary gear reduction unit 504 disposed within the longitudinal throughbore 114 of the handle 112. High pressure air is communicated via the air hose 180 coupled to the cover 170 at the proximal end 162 of the handle assembly 110 and directed into the motor 502. The air is routed through the motor body and directed against a plurality of vanes to rotate a rotor of the motor 502. The rotor includes an output shaft 503 coupled to the planetary gear reduction unit 504. The planetary gear reduction unit 504 serves to convert the high rotational speed of the rotor shaft to a drive coupling 506 that rotates at a lower speed but a higher torque output than the rotor shaft 503.

Figure 1:
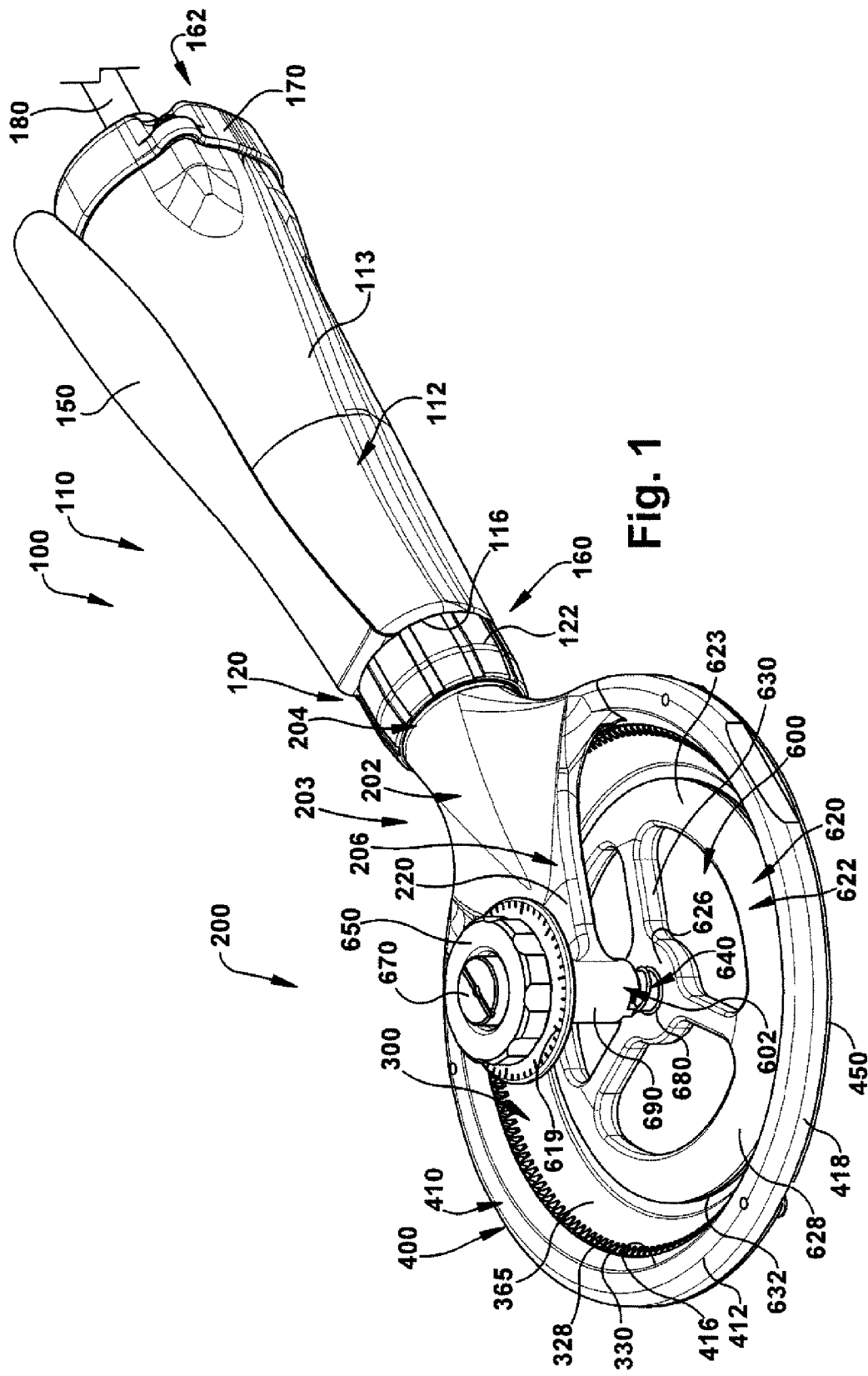
FIG. 1 is a schematic perspective view of a first exemplary embodiment of a hand held, power operated dermatome of the present disclosure including a handle assembly and a head assembly including a rotary knife blade and a depth gauge assembly extending into a central, interior region defined by the rotary knife blade.
Figure 2:
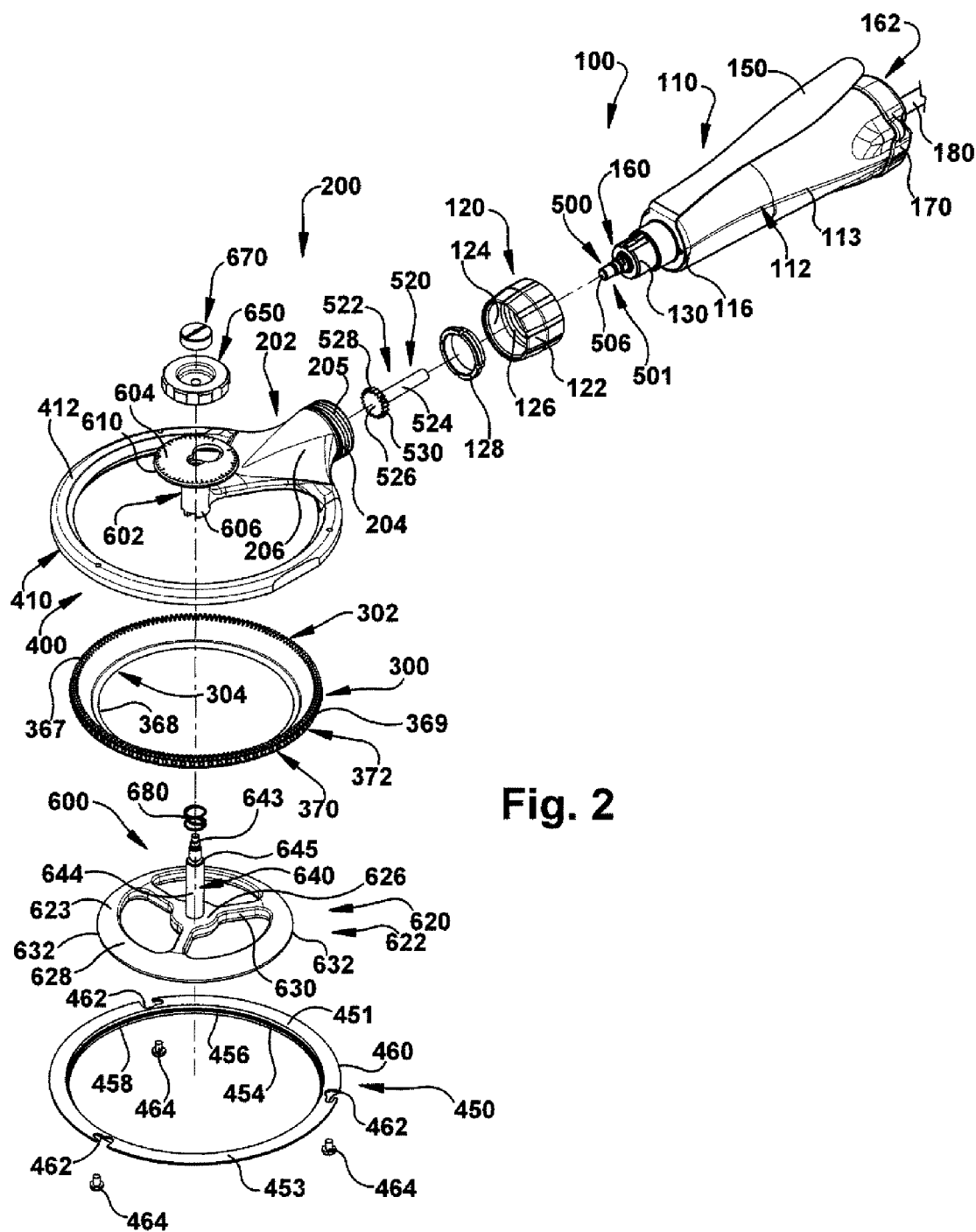
FIG. 2 is a schematic exploded perspective view of the power operated dermatome of FIG. 1.
Figure 3:
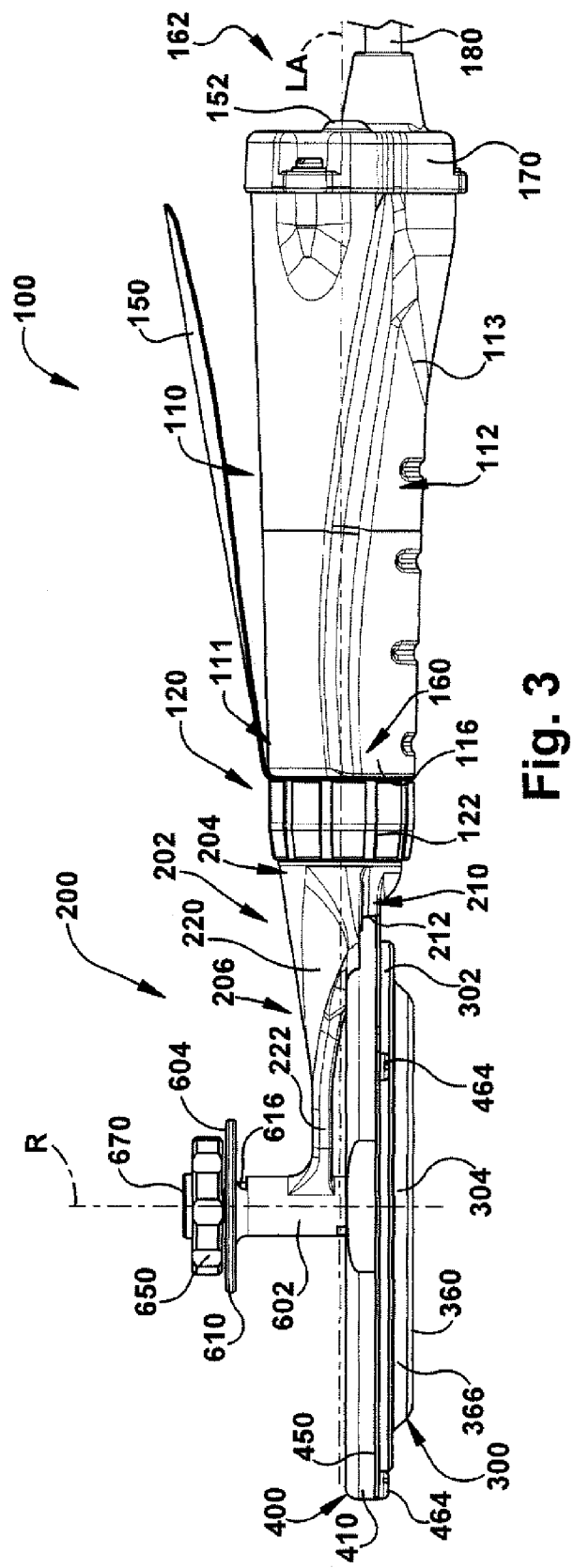
FIG. 3 is a schematic side elevation view of the power operated dermatome of FIG. 1.
Figure 4:
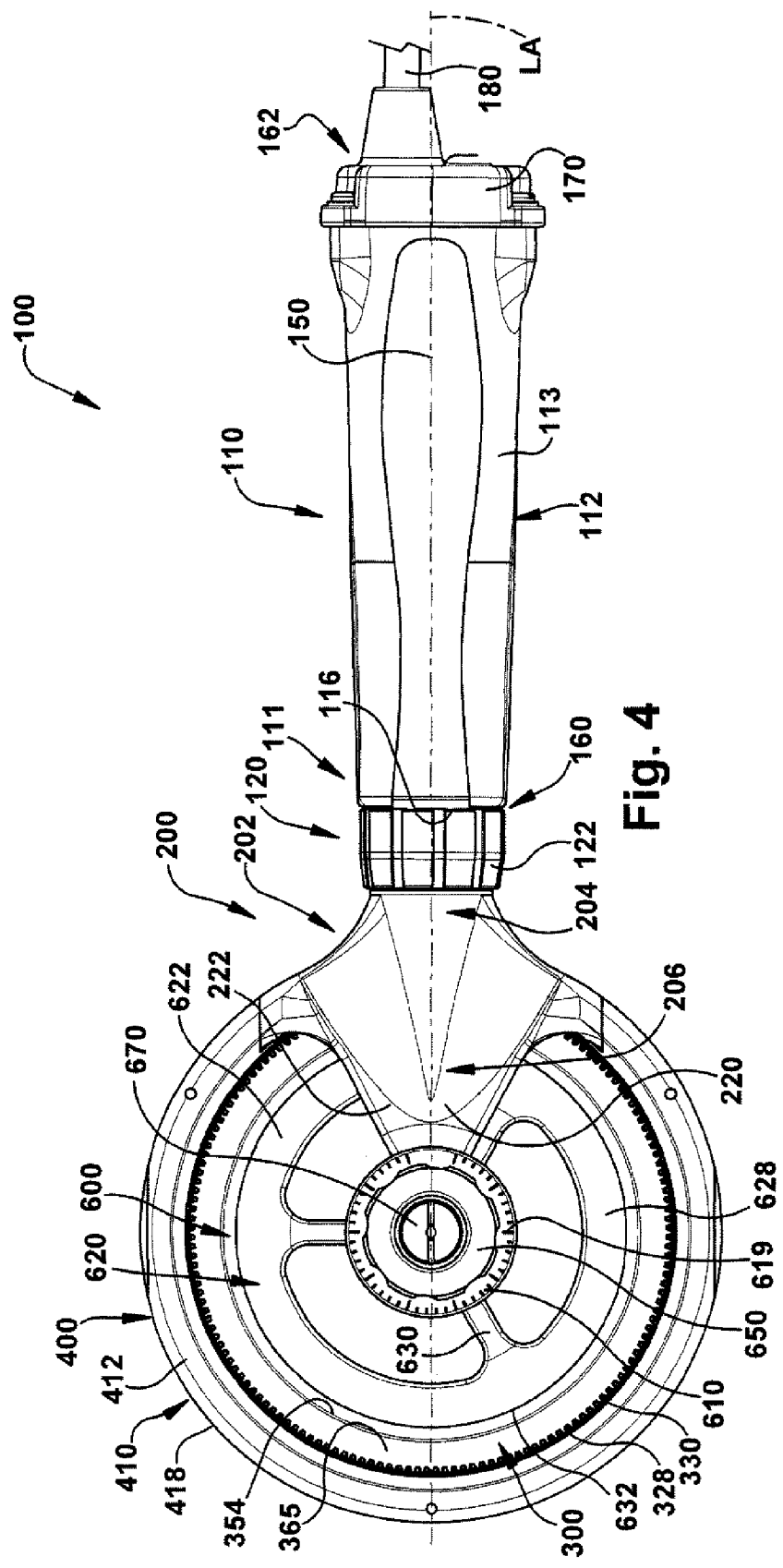
FIG. 4 is a schematic top plan view of the power operated dermatome of FIG. 1.

In one exemplary embodiment, the gear train 520 comprises a pinion gear 522 (FIG. 2). An input shaft 524 at a proximal end of the pinion gear 522 receives the drive coupling 506 of the drive motor assembly 501. The pinion gear 522 includes a gear head 526 at its distal end. In one exemplary embodiment, the gear head 526 defines a bevel gear 528 including a set of bevel gear teeth 530. The pinion gear 522 is supported for rotation in the gearbox housing 203 of the frame body 202 about a pinion gear axis of rotation PGR (FIG. 7) and is positioned such that the set of bevel gear teeth 530 of the pinion gear 522 meshes with a mating set of bevel gear teeth 330 of a driven gear 328 of the rotary knife blade 300. The gear head 526 of the pinion gear 522 engages and drives the driven gear of the rotary knife blade 300 to rotate the blade 300 about its axis of rotation R.

As can be seen in FIG. 7, the pinion gear axis of rotation PGR is substantially congruent with the handle assembly longitudinal axis LA. As the drive coupling 506 of the drive motor assembly 501 rotates the pinion gear 522 within the gearbox housing 203. Rotation of the pinion gear 522, in turn, rotates the rotary knife blade 300 about its axis of rotation R. A suitable pneumatic motor/planetary gear reduction unit configuration is disclosed in U.S. patent application Ser. No. 13/073,207 to Whited et al., filed Mar. 28, 2011, and entitled Power Operated Rotary Knife With Disposable Blade Support Assembly ("the '207 application"). The '207 application is assigned to the assignee of the present application and is incorporated herein, in its entirety, by reference.

Alternatively, the drive motor assembly 501 may comprise an external drive motor, for example, an external brushless DC servo motor, and a flexible shaft drive transmission (not shown). The drive motor assembly rotates a drive shaft of a flexible shaft drive transmission. A portion of the flexible shaft drive transmission extends through the longitudinal throughbore 114 of the elongated handle 112 of the handle assembly 110. A suitable DC motor/flexible drive shaft transmission configuration is disclosed in U.S. patent application Ser. No. 13/344,760 to Rapp et al., filed Jan. 6, 2012, and entitled Flex Shaft—Drive Motor Connection For Power Operated Rotary Knife ("the '760 application"). The '760 application is assigned to the assignee of the present application and is incorporated herein, in its entirety, by reference.

Alternately, the drive motor assembly 501 may comprise an electric drive motor disposed within the longitudinal thronghbore 114 of the handle 112. in one exemplary embodiment, the electric drive motor is a DC motor. A suitable DC electric motor, for example, the Maxon Model No. EC22 386680 and an associated gear reduction unit, for example, the Maxon Model No. GPM22M 305130, may be obtained from Maxon Motor AG, Sachsen, Switzerland (www-maxonmotor-com).

Head Assembly

Turning to FIGS. 8-13, the head assembly 200 of the power operated dermatome 100 of the present disclosure includes the frame body 202, the rotary knife blade 300, the annular blade housing assembly 400, and the depth gauge assembly 600. In the dermatome 100, both the depth gauge assembly 600 and the blade housing assembly 400 are supported by and extend from the frame body 202. The depth gauge plate 622 of the depth gauge assembly 600 extends into the interior region 301 of the rotary knife blade 300. A lower edge region 634 of the depth gauge plate 622, in combination with the cutting edge 360 of the rotary knife blade 300, determine the depth of cut DOC of the dermatome 100.

Frame Body 202

As best seen in FIGS. 8-13, the frame body 202 includes a rearward handle attachment portion 204 and a forward interface portion 206. The rearward handle attachment portion 204 comprises a generally cylindrical body 205 defining the threaded outer surface 230 of the frame body 202. The threaded outer surface 230 of the frame body cylindrical body 205 is engaged by the attachment assembly 120 to releasably affix the head assembly 200 to the handle assembly 110.

The frame body 202 includes a gearbox housing 203 which rotatably supports gear train 520 of the drive assembly 500, specifically, the pinion gear 522. The gearbox housing 203 includes an inner surface 208 of the frame body 202. The inner surface 208 defines a longitudinally extending throughbore 209. As seen in FIG. 7, the pinion gear 522 is seated in the throughbore 209. A front opening 232 (FIGS. 11 and 12) of the throughbore 209 is configured to allow the gear head 526 of the pinion gear 522 to engage the driven gear 328 of the rotary knife blade 300. A rear opening 234 (FIGS. 9 and 12) of the throughbore 209 allows entry of the drive coupling 506 of the drive motor assembly 501 into the pinion gear input shaft 524 when the head assembly 200 is releasably affixed to the handle assembly 110.

The forward interface portion 206 of the frame body 202 includes an upper interface region 220 that extends or transitions between the cylindrical body 205 of the rearward handle attachment portion 204 and the central cylindrical support 602 of the depth gauge assembly 600. In one exemplary embodiment, the upper interface region 220, when viewed from above in plan view, comprises a generally V-shaped rib 222 wherein the V-shaped rib 222 is widest adjacent to the cylindrical body 205 and tapers or converges in a direction proceeding toward the central cylindrical support 602, that is, the central cylindrical support 602 can be viewed as serving as a termination or vertex of the rib 222. Thus, the central cylindrical support 602 of the depth gauge assembly 600 is attached to and extends from the frame body 202 and, more specifically, the depth gauge assembly 600 is attached to and extends from the upper interface region 220 of the frame body 202.

Positioned axially below the upper interface region 220 is a lower interface region 210 that extends or transitions between the cylindrical body 205 of the rearward handle attachment portion 204 and the annular blade housing 410 of the blade housing assembly 400. In one exemplary embodiment, the lower interface region 210, when viewed from below in plan view, comprised a Y-shaped support 212 that includes arms that extend circumferentially about the annular blade housing 410. Thus, the annular blade housing 410 of the blade housing assembly 400 is attached to and extends from the frame body 202 and, more specifically, the lower interface region interface region 220 of the frame body 202.

Rotary Knife Blade 300

As can best be seen in FIGS. 14-17, in one exemplary embodiment, the annular rotary knife blade 300 includes an inner wall 365 and an outer wall 366 and a first upper end 367 and a second lower end 368. The inner wall 365 defines the open, interior region 301 of the rotary knife blade 300. The rotary knife blade 300 includes the upper body section 302, the lower blade section 304 and the continuous rolling bearing structure 370. The continuous rolling bearing structure 370 forms a portion of a peripheral outer surface 303 of the body section 302 and defines the convex bearing surface 380 of the rotary knife blade 300. The upper body section 302 extends between a first upper end 306 and a second lower end 308. The upper end 306 corresponds to and is congruent with the first upper end 367 of the rotary knife blade 300. A radially extending shoulder 308a between the body section 302 and the blade section 304 defines the second lower end 308 of the body 302. The body section 302 includes an inner wall 310 and a radially spaced apart outer wall 312. The first upper end 306 of the body section 302 defines the driven gear 328 of the rotary knife blade 300. The driven gear 328 comprises the set of bevel gear teeth 330 that operatively engage and mesh with the bevel gear 528 of the pinion gear 522, as previously discussed, such that rotation of the bevel gear 528 results in rotation of the rotary knife blade 300 about its axis of rotation R.

The body section 302 of the rotary knife blade 300 includes a bearing surface 319 formed in the outer wall 312 of the body 302. In one exemplary embodiment, the bearing surface 319 comprises a bearing race 320 that extends radially inwardly into the outer wall 312. The bearing race 320 includes a generally convex arcuate bearing face 322. The bearing face 322 provides a seating surface for the continuous rolling bearing structure 370 of the rotary knife blade 300. The continuous rolling bearing structure 370 defines the convex bearing surface 380 of the rotary knife blade 300 that projects radially outwardly from the outer wall 312 of the body section 302 of the blade 300 and thereby forms a portion of a peripheral outer surface 303 of the body section 302 and forms a portion of a peripheral outer surface 369 of the rotary knife blade 300. The continuous rolling bearing structure 370 rotationally supports the rotary knife blade 300 with respect to the blade housing assembly 400.

The continuous rolling bearing structure 370 comprises an annular rolling bearing strip 372 that extends continuously 360° around the periphery of the outer wall 312 of the body section 302 and is disposed in the bearing race 320. The rolling bearing strip 372 includes a plurality of spaced apart ball bearings 376 rotatably supported in radially spaced apart pockets of a separator cage 378. In one exemplary embodiment, the separator cage is flexible and a diameter of each of the ball bearings 376 is approximately 2 mm., although it should be understood that the diameter could be larger or smaller. Portions of the plurality of ball bearings 376 extend radially outwardly from the outer wall 310 of the blade body section 302 and thus form a part of the outer periphery 303 of the body section 302. Specific details concerning the structure and configuration of the plurality of spaced apart ball bearings and the flexible separator cage are disclosed in U.S. patent application Ser. No. 13/189,951, filed Jul. 25, 2011 to Whited et al., and entitled Power Operated Rotary Knife ("the '951 application"). The '951 application is assigned to the assignee of the present application and is incorporated herein, in its entirety, by reference.

The rolling bearing strip 372 is disposed in an annular gap G defined between opposing faces of the rotary knife blade 300, the blade housing 410 and a blade lock ring 450 of the blade housing assembly 400, in the region of the rotary knife blade bearing race 320. Specifically, the plurality of ball bearings 376 of the rolling bearing strip 372 are disposed within an annular passageway 374, which is circular in cross section and defined by the opposing arcuate bearing surfaces 319, 426, 458 of the rotary knife blade 300, the blade housing 410 and the blade lock ring 450, respectively.

By virtue of the annular rolling bearing strip 372 being continuous and disposed within the bearing race 320, the strip 372 is permanently affixed to and thus is part of the blade 300. However, as the plurality of ball bearings 376 of the rolling bearing strip 372 contact the blade bearing race 320, the rolling bearing may rotate with respect to the blade body 302 and the blade section 304 of the blade 300. When rotary knife blade 300 is rotated by the drive assembly 500 and, specifically, the pinion gear 522, at a specific, desired RPM, the separator cage 378 also moves or translates in a circle along the annular gap G, although the rotational speed of the separator cage 378 within the gap G is less than the RPM of the rotary knife blade 300. Thus, when the dermatome is in operation, the continuous, annular rolling bearing strip 372 traverses through the annular passageway 374 forming a circle about the knife blade axis of rotation R. Similarly, when the dermatome 100 is in operation, the separator cage 378, due to its movement or translation along the annular gap G about the knife blade axis of rotation R, can be considered as forming a complete cylinder within the gap G. Additionally, when the rotary knife blade 300 is rotated, the plurality of ball bearings 376 both rotate with respect to the separator cage 378 and also move or translate along the annular passageway 374 about the knife blade axis of rotation R as the separator cage 378 moves or translates along the annular gap G. A plane passing through the respective centers of the plurality of ball bearings 376 define a rotational plane RP (FIGS. 13 and 15) of the rotary knife blade 300. The rotational plane RP of the rotary knife blade 300 is substantially parallel to the cutting plane CP of the blade 300 and substantially orthogonal to the axis of rotation R of the blade 300.

The rotary knife blade 300 also includes the blade section 304 extending between a first upper end 350 (adjacent the shoulder 308a of the body section 302) and a second lower end 352. The second lower end 352 corresponds to and is congruent with the lower end 368 of the rotary knife blade 300. The blade section includes an inner wall 354 and a radially spaced apart outer wall 356. The inner and outer walls 354, 356 are generally parallel and frustoconical, converging in a direction proceeding downwardly or toward the cutting edge 360 of the blade. The cutting edge 360 of the rotary knife blade 300 is generally circular. The inner wall 310 of the body section 302 and the inner wall 354 of the blade section 304 combine to form the inner wall 365 of the rotary knife blade 300 and define the interior region 301 of the blade 300. The interior region 301 of the rotary knife blade is generally frustoconical, converging in a direction toward the cutting edge 360 of the blade 300. A plane aligned with the generally circular cutting edge 360 of the rotary knife blade 300 defines the cutting plane CP (FIG. 15) of the blade 300.

In one exemplary embodiment, the blade section 304 includes an upper region 358 and a lower region 359 separated by a knee or discontinuity between the two regions. Of course, it should be recognized that the blade section 304 may comprise a single region with no discontinuity. The lower region 359 defines the cutting angle CA of the blade and is defined by an angle between the inner wall 354 in the lower region 359 of the blade section 304 and the cutting plane CP. In one exemplary embodiment, the cutting angle CA is approximately 30°, although it should be understood that the cutting angle CA could be greater or smaller. As can be best seen in FIG. 16, the lower end 352 of the blade section 304 which defines the cutting edge 360, includes a short section of wall 362 bridging the inner and outer walls 354, 356. The cutting edge 360 is formed at the intersection of the short section of wall 362 and the inner wall 354. The short section of wall 362 is slightly angled with respect to the cutting plane CP, at about 5° in one exemplary embodiment, to provide relief for the cutting edge 360.

In one exemplary embodiment, the inner diameter (defined by the cutting edge 360) of the rotary knife blade 300 is approximately 4.000 in., while the outer diameter (defined by the outer periphery of the plurality of ball bearings 376 the rolling bearing strip 372 is approximately 5.189 in., although it should be understood that the diameters could be larger or smaller.

Blade Housing Assembly 400

As can best be seen in FIGS. 10-13 and 16-17, the blade housing assembly 400 includes the annular blade housing 410 and the blade lock ring 450. The annular blade housing 410 extends from and is supported by the Y-shaped support 212 of the lower interface region 210 of the forward interface portion 206 of the frame body 202. The blade housing 410 includes a first upper end 412 and an axially spaced apart second lower end 414. The blade housing 410 further includes an inner wall 416 and a radially spaced apart outer wall 418. The blade housing 410 includes three peripherally spaced apart threaded openings 430 of the blade housing 410. The three threaded openings 430 extend from the second lower end 414 through the first upper end 412. The inner wall 416 of the blade housing 410 includes a bearing surface 420. In one exemplary embodiment, the bearing surface 420 comprises a bearing race 422 that extending radially inwardly into the inner wall 416 of the blade housing 410. The bearing race 422 includes the concave, arcuate bearing surface or face 426.

Figure 13:
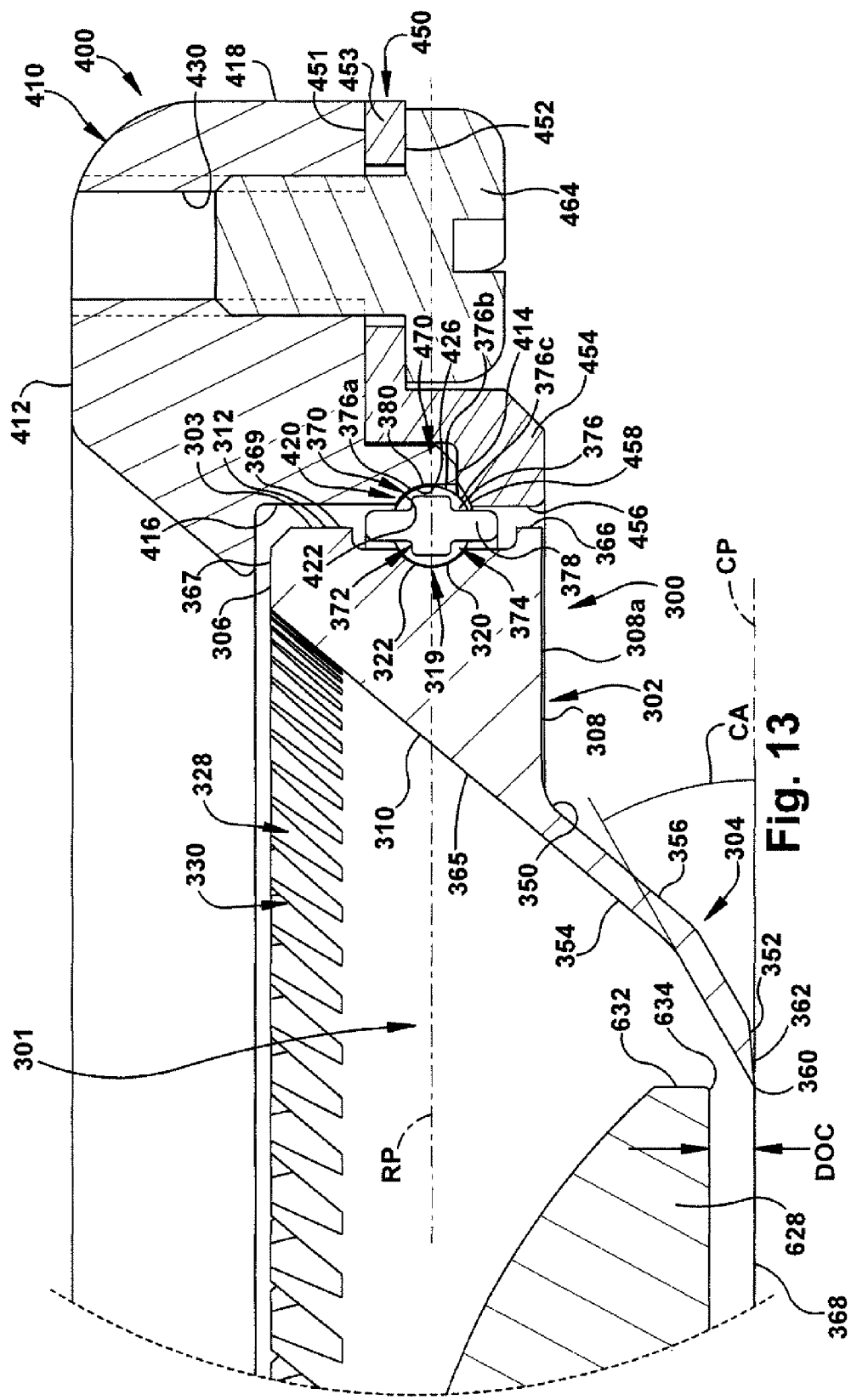
FIG. 13 is a schematic enlarged section view of a portion of the head assembly of FIG. 8 that is within a dashed circle labeled FIG. 13 in FIG. 12.

As can be best be seen in FIGS. 13, 17 and 18, in axial extent, the arcuate bearing face 426 is a curved bearing surface that extends from an upper region 376a of the ball bearing 376 and generally conforms to the curvature of the ball bearing 376 to about a midpoint 376b of the ball bearing 376. The arcuate bearing face 426 does not, however, extend all the way to a lower region 376c of the ball bearing 376. Instead, an arcuate bearing surface or face 458 formed on an inner surface 456 of the blade lock ring 450 constitutes a portion of a total bearing race 470 (FIGS. 17 and 18) provided by the blade housing assembly 400. The total bearing race 470 defined by the blade housing assembly 400 results from a combination of the bearing surfaces of the blade housing 410 and the blade lock ring 450, specifically, the arcuate bearing face 426 of the blade housing 410 and the arcuate bearing face 458 of the blade lock ring 450. The total bearing race 470 serves as an arcuate bearing surface for the annular rolling bearing strip 372 of the rotary knife blade 300 when the blade lock ring 450 is secured to the blade housing 410 and the rotary knife blade 300 is captured or sandwiched therebetween.

The blade lock ring 450 includes an upper surface 451 and a lower surface 452 and comprises an upper seating region 453 and a radially inwardly offset lower bearing region 454. The upper seating region 453 seats flush against the blade housing 410 and includes three peripherally spaced apart slots 462 in an outer periphery 460 of the blade lock ring 450. The blade lock ring 450 adapted to be secured to a stepped shoulder 415 (FIG. 18) near the lower end 414 of the blade housing 410. The blade lock ring 450 is secured to the stepped shoulder 415 of the blade housing 410 via three threaded fasteners 464, each of which passes through a correspond peripherally spaced apart slot 462 in an outer periphery 460 of the blade lock ring 450.

To install or affix the rotary knife blade 300 to the blade housing assembly 400, with the blade lock ring removed, the head assembly 200 is turned upside down and the rotary knife blade 300 is placed in the upside down blade housing 410. The plurality of ball bearings 376 of the rotary knife blade 300 rest on the bearing race 422 of the blade housing 410 thereby the rotary knife blade 300 is supported by the blade housing 410. The three slots 462 of the blade lock ring 450 are aligned with the threaded openings 430 of the blade housing 410. The three threaded fasteners 464 pass through the slots 462 and are threaded into the threaded openings 430 of the blade housing 410 to complete the installation. Because of the configuration of the three slots 462, it is only necessary to loosen the three threaded fasteners 464 a sufficient amount to rotate the blade lock ring 450 with respect to the blade housing 410. This allows the blade lock ring 450 to be removed from the blade housing 410 without removing the three threaded fasteners 464 from the threaded openings 430 of the blade housing 410. When the blade lock ring 450 is removed from the blade housing 410 turning the head assembly 200 upside down causes the rotary knife blade 300 to fall out of the blade housing 410 thereby removing the blade 300 from the blade housing assembly 400.

Depth Gauge Assembly 600

Figure 10:
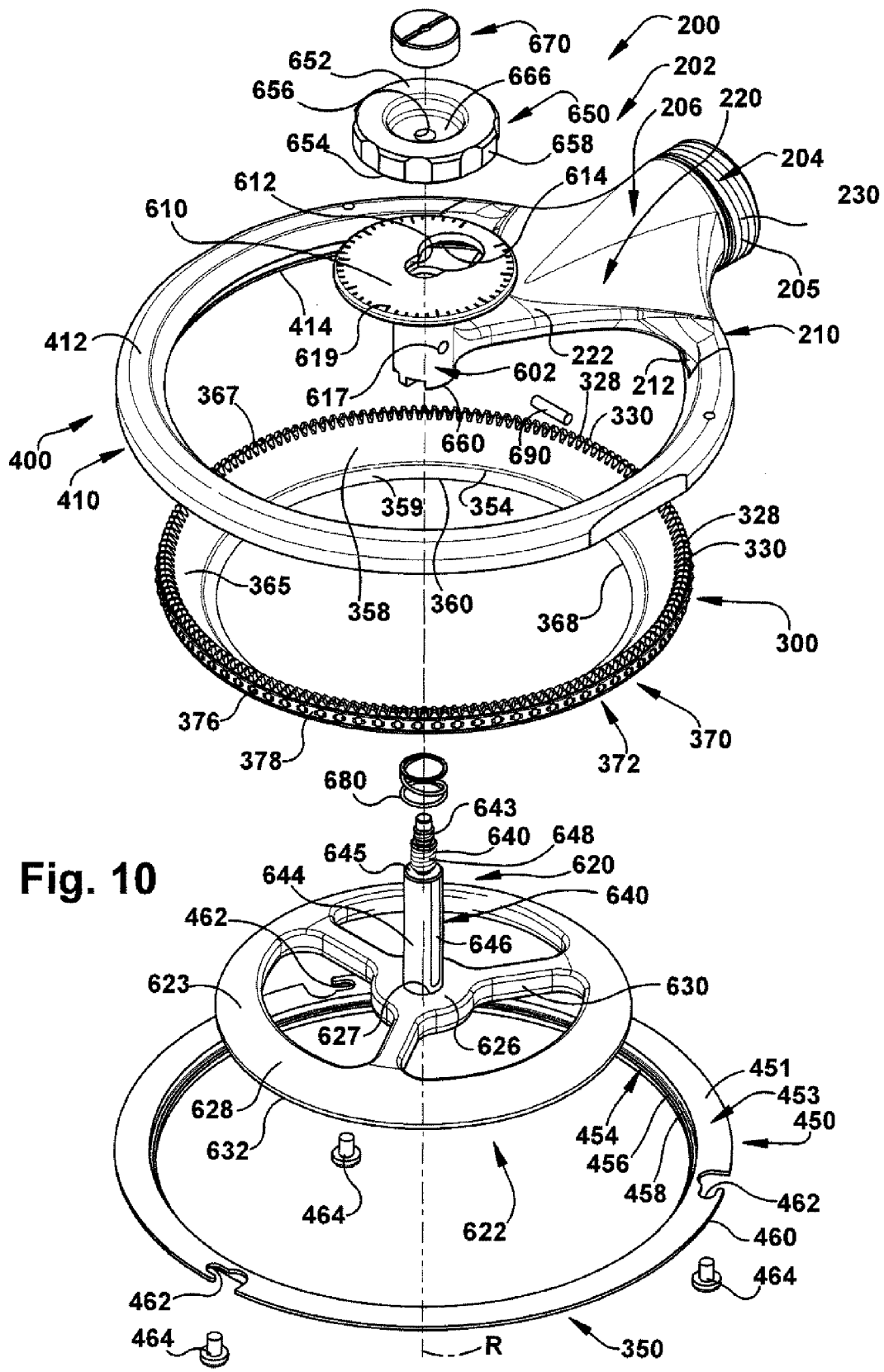
FIG. 10 is a schematic exploded top perspective view of the head assembly of FIG. 8.
Figure 11:
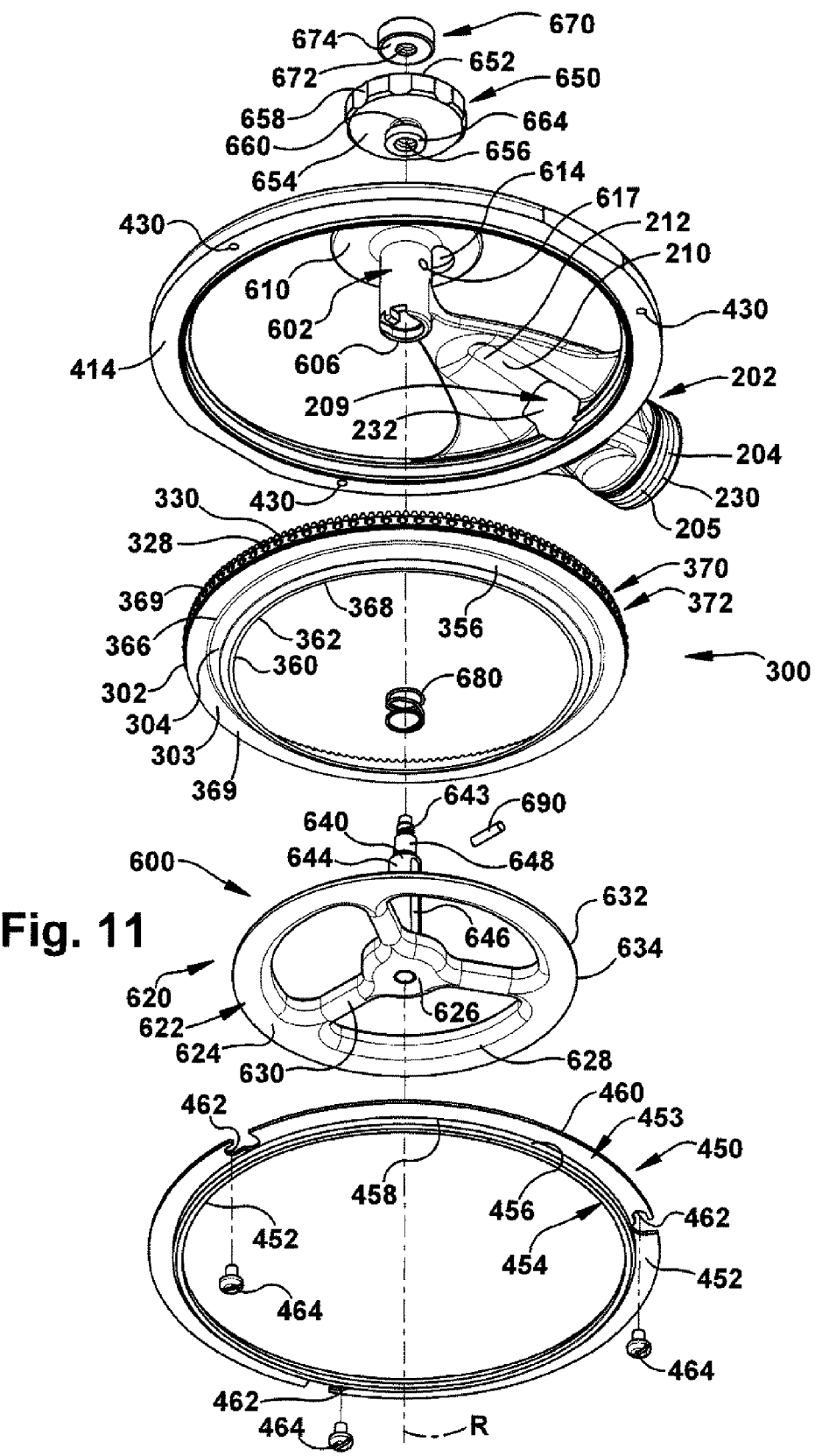
FIG. 11 is a schematic exploded bottom perspective view of the head assembly of FIG. 8.

As can best be seen in FIGS. 10-13 and 17-21, the depth gauge assembly 600 includes the depth gauge support 602 and the depth gauge 620. The depth gauge 620 includes the depth gauge shaft 640 and the depth gauge plate 622. The depth gauge assembly 600 further includes the depth adjustment knob 650, a stop ring 670, a biasing spring 680 and a dowel pin 690 (FIGS. 10 and 11). Advantageously, the depth gauge assembly 600 permits an operator to quickly and accurately change the depth of cut DOC of the dermatome from essentially 0.000 in. (no depth of cut of skin tissue ST—shown schematically in FIG. 21) to 0.045 in. (full depth of cut of skin tissue ST—shown schematically in FIGS. 12 and 20). Obviously, the range of depth of cut DOC may be changed based on the configuration of the depth gauge assembly 600 and the present invention is not limited to the exemplary depth of cut range set forth herein. As changing the depth of cut DOC of the dermatome 100 is accomplished by rotation of the depth adjustment knob 650, the depth of cut DOC is infinitely variable between the 0.000 in. and 0.045 in. endpoints. That is, the operator can precisely dial in an exact desired depth of cut DOC for the dermatome 100.

Depth Gauge Cylindrical Support 602

As best seen in FIGS. 8 and 10-12, the depth gauge cylindrical support 602 extends from and is supported by the V-shaped rib 222 of the upper interface region 220 of the forward interface portion 206 of the frame body 202. The depth gauge support 602, in one exemplary embodiment, is generally cylindrical and includes an upper end 604 and an axially spaced apart lower end 606. The depth gauge cylindrical support 602 defines an axially extending central opening 608 (FIG. 12) passing through the support 602. A radially outwardly extending flange 610 is disposed at the upper end 604 of the depth gauge cylindrical support 602. As can be seen in FIG. 10, the flange 610 includes a first smaller opening 612 that is axially aligned with the central opening 608 and a second larger opening 614 that is connected to but offset from the first smaller opening 612. A radially outwardly extending slot 616 (FIG. 12) is disposed between the flange 610 and the central opening 608 of the depth gauge cylindrical support 602.

An upper surface 618 of the flange 610 includes indicia or markings 619 (FIG. 10) representing gradations for the depth of cut DOC of the dermatome 100 as the depth adjustment knob 650 is rotated. Specifically, each of the smaller gradations represent a change in the set depth of cut DOC of 0.001 in., while the larger gradations represent a change in the set depth of cut of 0.005 in. The indicia 619 facilitate precise setting of the dermatome depth of cut DOC by the operator.

The depth gauge shaft 640 is received in the axially extending central opening 608 of the cylindrical support 602. The depth gauge shaft 640 is supported by the cylindrical support 602 for axial movement with respect to the cylindrical support 602. Specifically, the cylindrical support 640 contacts and supports the depth gauge shaft 640 over an axial length labeled AL in FIG. 12. In one exemplary embodiment, the axial length AL of the cylindrical support 602 is approximately 1.05 in., while the overall axial length of the cylindrical support 602 extending between the upper end 604 of the cylindrical support 602 and the lower end 606 of the cylindrical support 602 is approximately 1.25 in.

Depth Gauge 620

Figure 12:
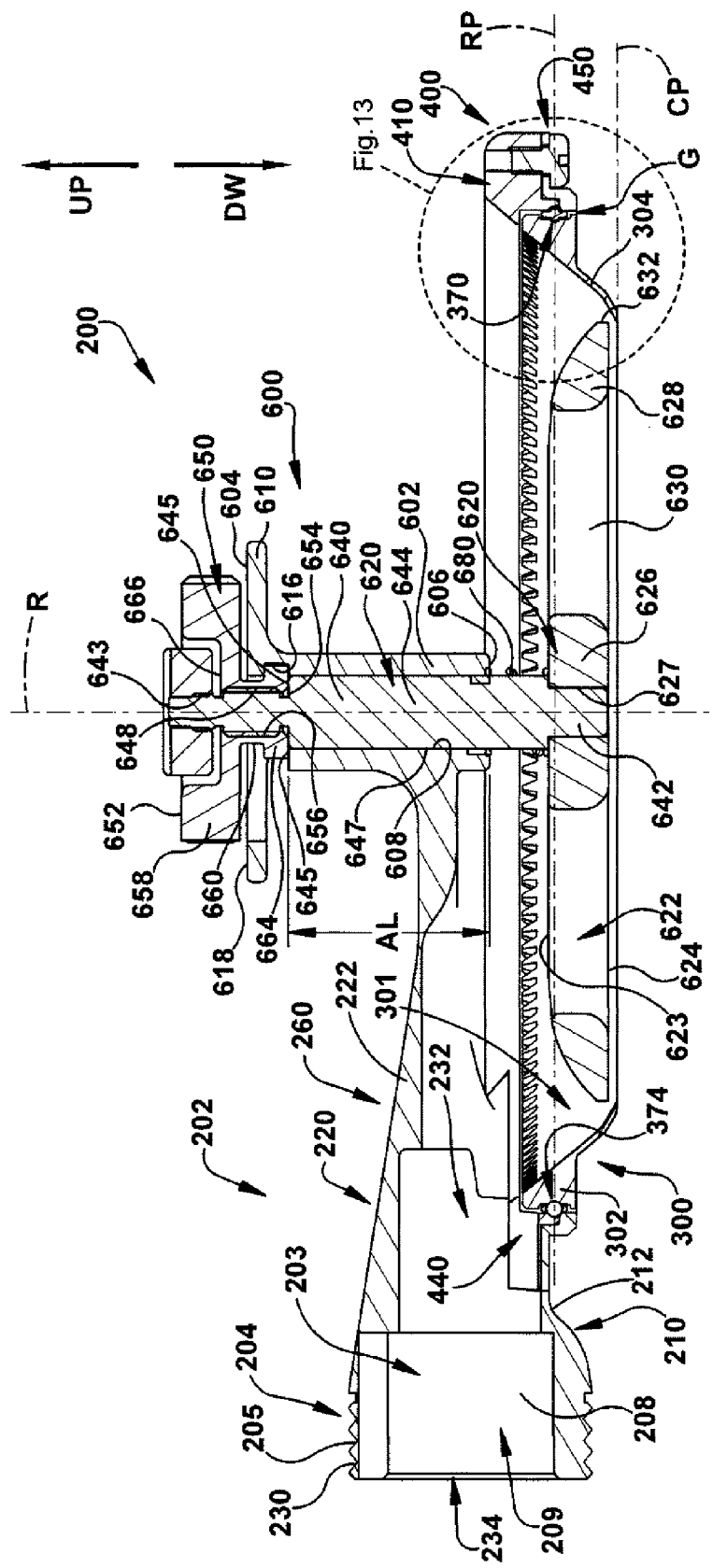
FIG. 12 is a schematic section view of the head assembly of FIG. 8 as viewed from a plane indicated by the line 12-12 in FIG. 9.

The depth gauge 620 is supported by the depth gauge support 602 and includes the depth gauge plate 622 and the depth gauge shaft 640. As can be seen in FIG. 12, the depth gauge shaft 640 and the depth gauge plate 622 are substantially concentric with the knife blade axis of rotation R. The depth gauge 20 is adjustable to move axially along the axis of rotation R, that is, the depth gauge moves axially respect to the depth gauge support 602 and with respect to the cutting plane CP of the rotary knife blade 300. Movement of the depth gauge plate 622 with respect to the cutting plane CP of the rotary knife blade 300 changes the dermatome depth of cut DOC. The depth gauge plate 622 and a portion of the depth gauge shaft 640 extend into the interior region 301 of the rotary knife blade 300. The depth gauge 620 also includes the stop ring 670 which is affixed to an upper end of the depth gauge shaft 640 and moves with the shaft 640 axially to limit downward movement of the depth gauge 620. That is, the stop ring 670 insures that the minimum depth of cut DOC is 0.000 in., as opposed to the depth gauge plate 622 moving in a downward direction DW to a negative depth of cut DOC position.

Depth Gauge Plate 622

The depth gauge plate 622 is generally disc-shaped and includes an upper surface 623 and an axially spaced apart generally planar lower surface 624. The depth gauge plate 622 includes a central body 626 and a radially outwardly spaced annular rim 628. The central body 626 and the annular rim 628 are connected by three radially extending ribs 630. The central body 626 of the depth gauge plate 622 includes a central opening 627 that receives a lower connecting end 642 of the depth gauge shaft 640 to secure the depth gauge plate 622 to the depth gauge shaft 640.

The depth gauge plate 622 includes a radially outer peripheral surface 632. A lower edge region 634 of the depth gauge plate 622 is an intersection region between the planar lower surface 624 of depth gauge plate 622 and outer peripheral surface 632 of depth gauge plate. At any axial position of the depth gauge plate 622, the lower edge region 634 of the depth gauge plate 622 is the closest portion of the depth gauge 622 to the cutting edge 360 of the rotary knife blade 300. The lower edge region 634 is nearly (but not exactly) axially aligned with the rotary knife blade cutting edge 360. As such, an axial distance between the lower edge region 634 of the depth gauge plate 622 and the cutting edge 360 of the rotary knife blade 300 determines the depth of cut DOC of the dermatome 100. Recall that the cutting edge 360 defines the cutting plane CP of the rotary knife blade 300, therefore, stated another way, an axial distance AD (FIG. 18) between the lower edge region 634 of the depth gauge plate 622 and the cutting plane CP of the rotary knife blade 300 determines the depth of cut DOC of the dermatome 100.

Depth Gauge Shaft 640

As best seen in FIG. 12, the depth gauge shaft 640 is generally cylindrical and includes the lower connecting end 642 that is received in the central opening 627 of the central body 626 of the depth gauge plate 622 to attach the depth gauge shaft 640 and the depth gauge plate 622. The depth gauge shaft 640 includes a reduced diameter threaded upper portion 643. When the depth gauge shaft 640 is inserted into the axially extending central opening 608 of the depth gauge support 602, first, the second threaded portion 648 of the depth gauge shaft 640 is threaded into the central threaded opening 656 of the depth adjustment knob 650, then, the stop ring 670 is threaded onto the upper threaded portion 643 of the depth gauge shaft 640 to secure the depth gauge shaft 640 (and attached depth gauge plate 622) to the depth gauge support 602. When it is desired to remove the depth gauge shaft 640 from the depth gauge support 602, the stop ring 670 is unthreaded and removed from the depth gauge shaft 640 and the depth gauge shaft 640 is unthreaded from the central threaded opening 656 of the depth adjustment knob 650, allowing the depth gauge shaft 640 to drop out of the depth gauge support 602 for cleaning/sterilization purposes.

The depth gauge shaft 640 includes an outer surface 647 defining an axially extending slot 646. The axially extending slot 646 receives the dowel pin 690 (FIGS. 10 and 11) that passes through a radial opening 617 in the depth gauge cylindrical support 602 to prevent relative rotation between the depth gauge shaft 640 as supported within the cylindrical support 602. The depth gauge shaft 640 also includes a second threaded portion 648 that is disposed below the threaded upper portion 643. The second threaded portion 648 of the depth gauge shaft 640 is threadedly received in a threaded central opening 656 of the depth adjustment knob 650.

Depth Adjustment Knob 650

The depth adjustment knob 650 includes an upper end 652 and a lower end 654. The depth adjustment knob 650 includes a central threaded opening 656 which is threaded onto the second threaded portion 648 of the depth gauge shaft 640. The dowel pin 690 and the axially extending slot 646 of the depth gauge shaft 656 allow the depth gauge shaft 656 to move axially within the axially extending central opening 608 of the depth gauge cylindrical support 602. The depth adjustment knob 650, when rotated, drives the depth gauge shaft 656 upward or downward with respect to the depth gauge cylindrical support 602.

The depth adjustment knob 650 includes a central stem 660, an enlarged upper head 658 above the stem 660, and an enlarged lower head 664 below the stem 660. The enlarged lower head 664 is sized to pass though the larger offset opening 614 of the flange 610 of the depth gauge cylindrical support 602 and is received in the slot 616 of the cylindrical support 602 to restrain axial movement between the depth adjustment knob 650 and the cylindrical support 602. The enlarged upper head 658 of the depth adjustment knob 650 includes a recessed contact surface 666 that is configured to be contacted by a lower surface 674 of the stop ring 670. An upper surface of the enlarged upper head 658 will include an arrow or some other marking that can be aligned with the indicia 619 marked on the upper surface 618 of the cylindrical support flange 610 to aid the operator in adjusting and setting the depth of cut DOC of the dermatome 100.

As the depth adjustment knob 650 is rotated by the operator, the dowel pin 690 extending into the axially extending slot 646 prohibits the depth gauge shaft 640 and the depth gauge plate 622 from rotating with the depth adjustment knob 650. The dowel pin/axially extending slot configuration 690/646 does permit the depth gauge shaft 640 to move up and down axially within the depth gauge cylindrical support 602 to change the depth of cut DOC of the dermatome 100. However, the depth gauge shaft 640 is constrained from rotating with the depth adjustment knob 650 by virtue of the dowel pin 690 fitting into the axially extending slot 646. The depth gauge shaft 640 is constrained from rotating with the depth adjustment knob 650 and the knob 650 is constrained from axial movement by virtue of the enlarged lower head 664 of the knob 664 being confined in the radially outwardly extending slot 616 of the depth gauge cylindrical support 602. Thus, rotation of the depth adjustment knob 650 drives the depth gauge shaft 640 axially in the upward direction UP or the downward direction DW with respect to the depth gauge cylindrical support, depending on the direction of rotation of the depth adjustment knob 650.

When depth adjustment knob 650 is rotated to move the depth gauge 620 in the downward direction DW, the dowel pin 690 prevents rotation of the depth gauge 620 with the depth adjustment knob 650. Thus, depending on the direction of rotation of the depth adjustment knob 650, the depth gauge 620 will be moved in the upward direction UP or the downward direction DW with respect to the cylindrical support 602 and the rotary knife blade 300. Movement of the depth gauge 620 in the upward direction is limited by contact between the upper surface 645 of the central portion 644 of the depth shaft 640 and a lower end 654 of the depth adjustment knob 650 such that a maximum depth of cut DOC is 0.045 in. This maximum depth of cut DOC configuration is shown in FIGS. 12 and 13 and is referred to as the fully open position of the dermatome 100.

Figure 21:
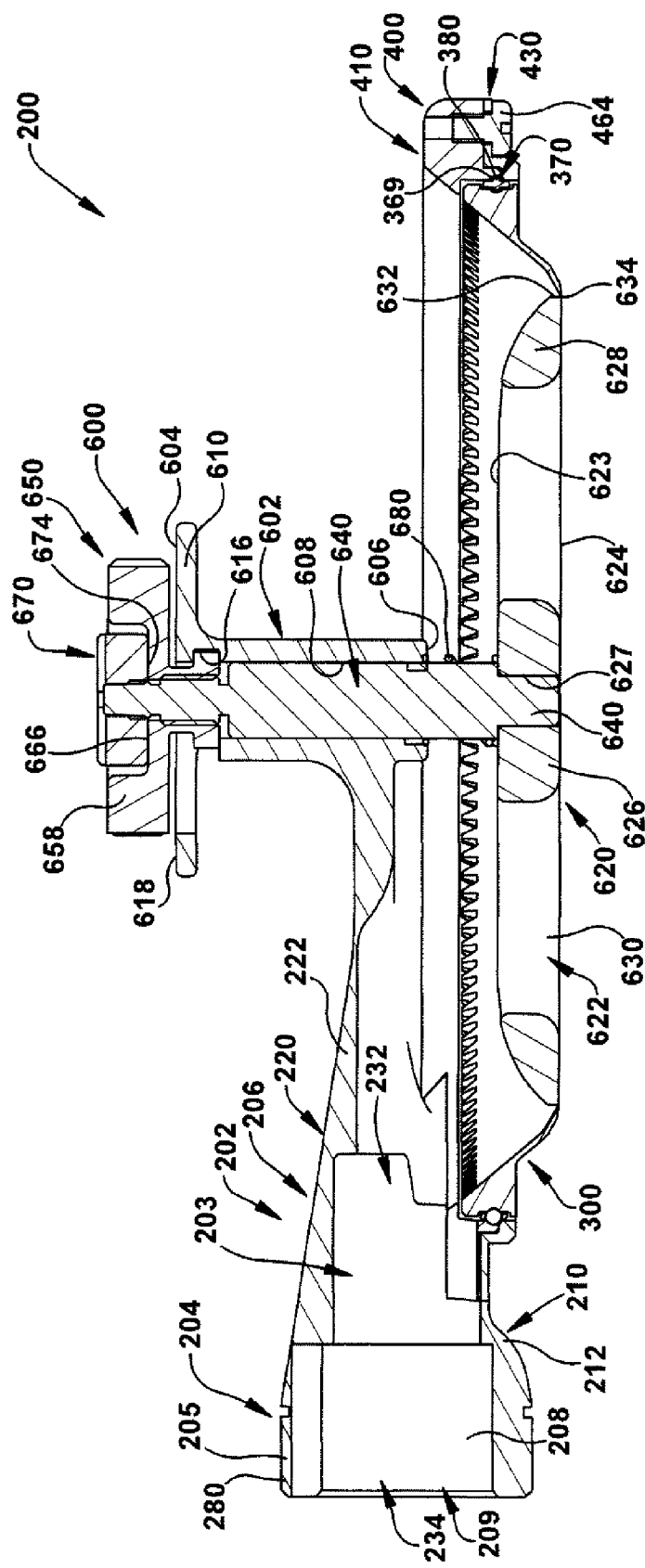
FIG. 21 is a schematic section view of a portion of the dermatome of FIG. 1 showing the depth gauge assembly in a fully closed position providing a minimum depth of cut of the dermatome.

Movement of the depth gauge in the downward direction DW is limited by contact between the lower surface 674 of the stop ring 670 and the recessed contact surface 666 of the enlarged upper head 658 of the depth adjustment knob 650. This minimum depth of cut DOC configuration is shown in FIG. 21 and is referred to as the fully closed position of the dermatome 100. The biasing spring 680 is trapped between the central body 626 of the depth gauge plate 622 and the lower end 606 of the depth gauge cylindrical support 602 to bias the depth gauge 620 to the fully closed position.

In one exemplary embodiment, the handle assembly 110 may be fabricated of plastic or other material or materials known to have comparable properties and may be formed by molding and/or machining. The attachment assembly 120, the frame body 202, and the depth gauge assembly 600 may be fabricated of aluminum or stainless steel or other material or materials known to have comparable properties and may be formed/shaped by casting and/or machining. The rotary knife blade 300 and the blade housing assembly 400 may be fabricated of a hardenable grade of alloy steel or a hardenable grade of stainless steel, or other material or materials known to have comparable properties and may be formed/shaped by machining, forming, casting, forging, extrusion, metal injection molding, and/or electrical discharge machining or another suitable process or combination of processes.

Operation of Dermatome 100

FIGS. 17-19 schematically illustrate use of the dermatome 100 of the present disclosure for excising a layer skin tissue ST in a donor grafting region GR and, in particular, obtaining a thin type, split thickness skin graft wherein a depth of a layer of skin tissue being excised from the graft region GR is on the order of 0.005 in. to 0.012 in. FIG. 17 schematically shows the initial incision into an upper layer or surface SST of the skin tissue ST with the dermatome 100. Recall that in the illustrated and exemplary embodiment, the cutting angle CA of the rotary knife blade 300 is approximately 30°. In making the incision into the skin tissue surface SST, the angle of the dermatome 100 is manipulated such that a skin tissue cutting angle STCA is shallower than the cutting angle CA of the knife blade 300. In one exemplary embodiment, the cutting angle of the inner wall 310 in the lower region 359 of the blade section 304 adjacent the cutting edge 360 with respect to the surface SST of the skin tissue ST being excised lower is approximately 15°. Thus, the skin tissue cutting angle STCA (approximately 15° )is less than the blade cutting angle CA. (approximately 30°). Thus, the outer wall 418 of the blade housing 410 is not vertical, but rather is slightly angled downwardly toward the skin tissue ST.

FIG. 18 schematically shows the cutting or excising of the skin tissue ST. As the actuated dermatome 100 moves along a path of travel PT, the dermatome 100 produces an excised section of skin tissue EST which flows along the inner wall 365 and through the central interior region 301 of the rotary knife blade 300 and slanted or frustoconical upper portion of the blade housing inner wall 416. The slanted upper portion of the blade housing inner wall 416 generally continues the frustoconical inner wall 365 of the rotary knife blade 300. The excised section of skin tissue EST is a flexible, generally rectangular piece or section of skin tissue ST that exits the dermatome 100 by moving or "flopping" (since the skin tissue is flexible or flaccid) over the upper end or wall 412 of the blade housing 410. As schematically depicted in FIG. 18, a longitudinal extent LE of the excised section EST, a depth or thickness of excised skin tissue DEST should be uniform and should conform in thickness to the depth of cut DOC set by the operator of the dermatome 100. In moving along the path of travel PT, the angle of the dermatome 100 is held relatively flat, that is, the skin tissue cutting angle STCA is approximately equal to the rotary knife blade cutting angle CA. The skin tissue cutting angle STCA and the rotary knife blade cutting angle CA both being approximately 30°. Advantageously, the operator need only keep the cutting plane CP of the dermatome 100 flush or flat against the surface SST of the skin tissue ST as the dermatome 100 is moved along its path of travel PT to excise a section of skin tissue EST. Thus, with the dermatome 100 of the present disclosure, undertaking a successful excising procedure which results in an excised skin tissue section EST having a consistent and desired depth or thickness is more straightforward and less dependent on operator skill level.

FIG. 19 schematically shows the termination of the excising procedure, that is, ending of the cutting of the skin tissue ST in the grafting region GR with the dermatome 100. Like with the incision, the dermatome 100 is manipulated by the operator to have a shallower skin tissue cutting angle STCA of approximately 15°. This shallow skin tissue cutting angle STCA causes the blade 300 to tend to move upwardly through the skin tissue SK. If necessary, the operator can slightly wiggle the dermatome 100 in a side-to-side motion to facilitate the rotary knife blade in cutting upwardly and through the surface of the skin tissue ST. When the blade 300 comes through or emerges from the surface SST of the skin tissue ST, this terminates the cut or excision and determines or fixes the total longitudinal extent LE of the excised skin tissue section EST.

FIG. 20 schematically depicts the excising of a thicker layer of skin tissue ST with the dermatome 100. Here, the dermatome 100 is used for obtaining a full thickness skin graft from a donor graft region GR wherein a depth of a layer DEST of skin tissue EST being excised from a donor graft region GR is on the order of 0.030 in. to 0.043 in.

It should be understood by one of ordinary skill in the art that an apparatus described as the dermatome 100 could be adapted and utilized for a wide variety of other medical applications including, but not limited to, soft tissue harvesting and/or removal, bone harvesting and/or removal, dermatological treatment needs, and other medical procedures.

Second Exemplary Embodiment-Power Operated Dermatome 1000

Figure 22:
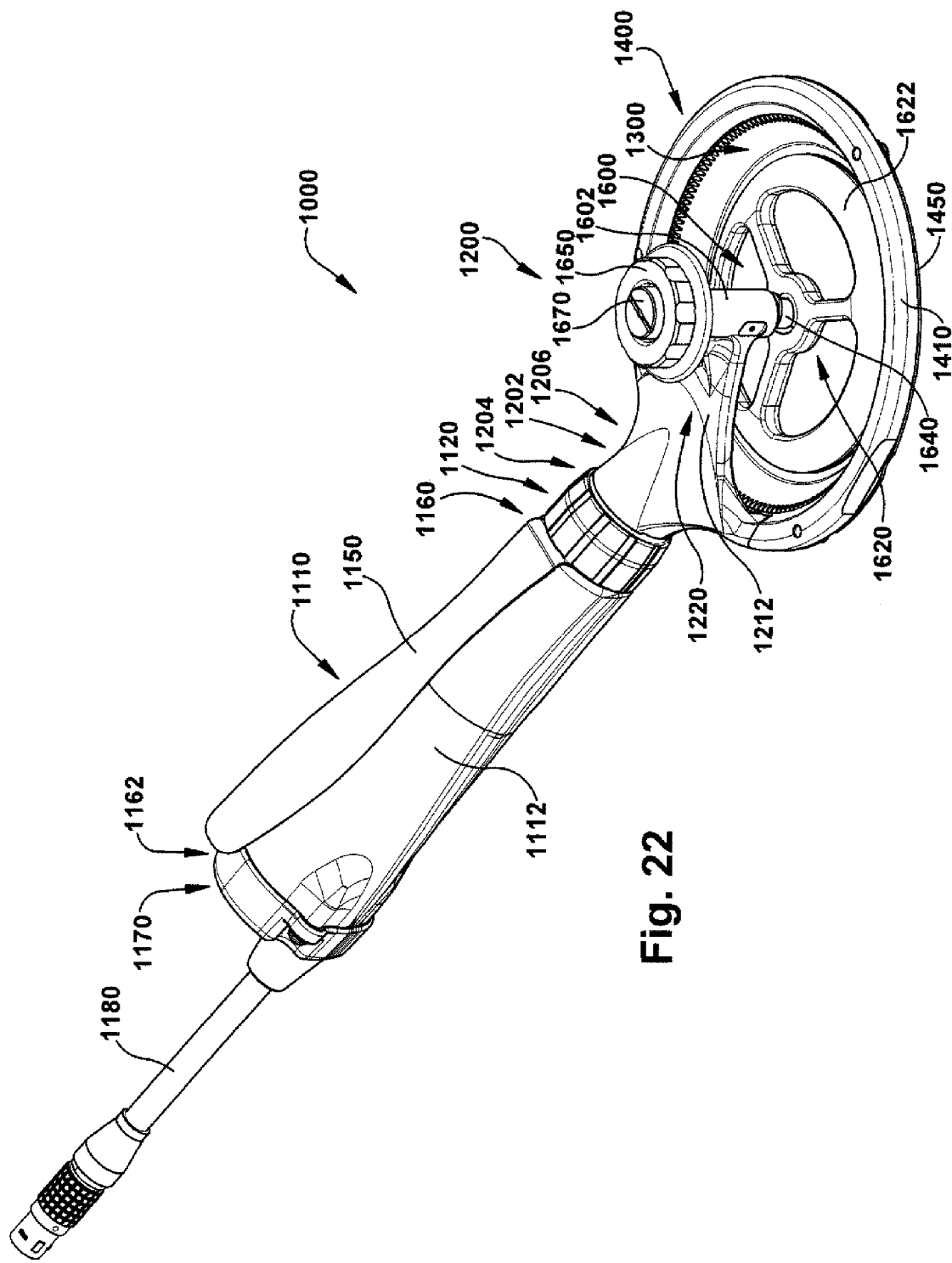
FIG. 22 is a schematic perspective view of a second exemplary embodiment of a hand held, power operated dermatome of the present disclosure including a handle assembly and a head assembly including a rotary knife blade and a depth gauge assembly extending into a central, interior region defined by the rotary knife blade.
Figure 23:
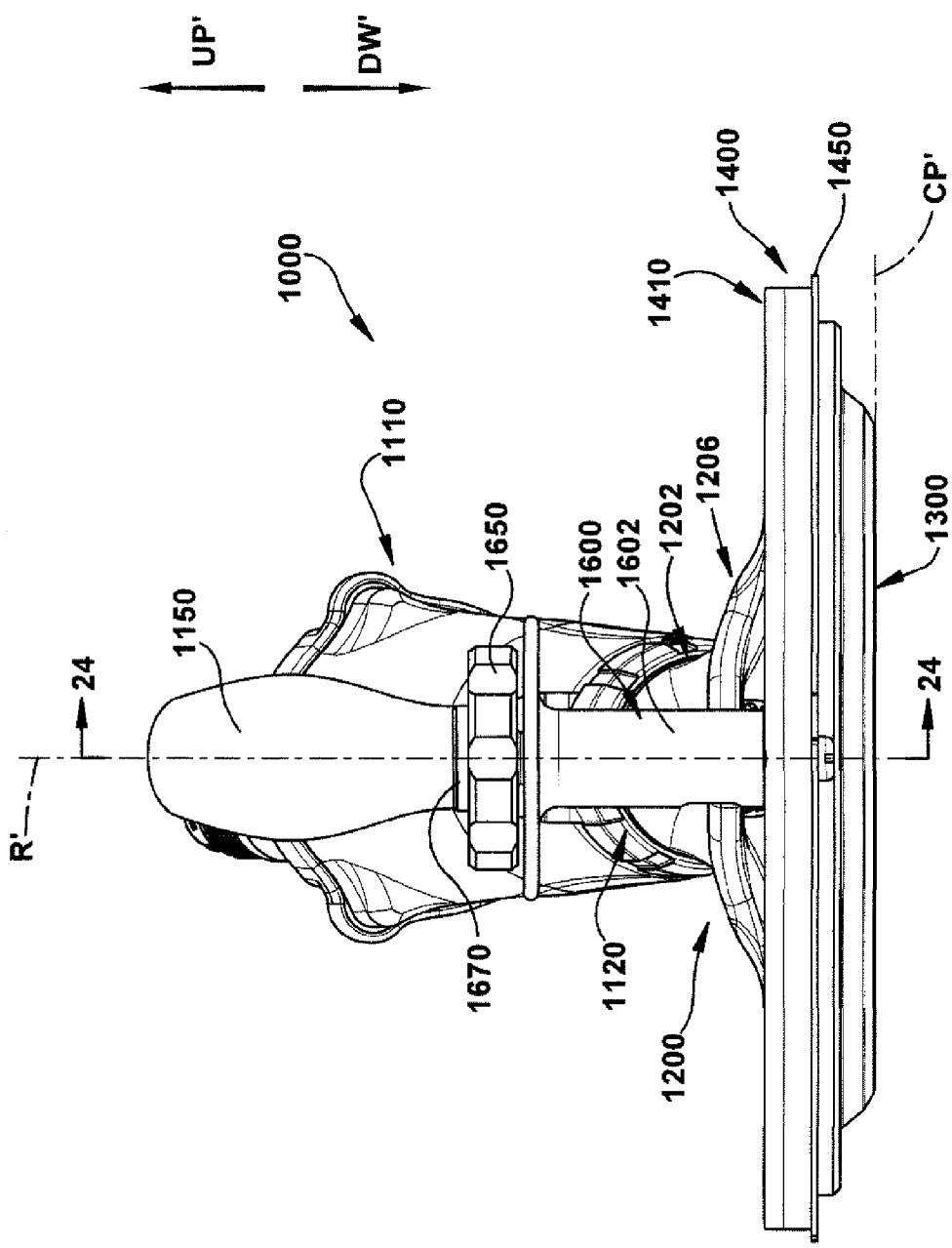
FIG. 23 is a schematic front elevation view of the power operated dermatome of FIG. 22.
Figure 24:
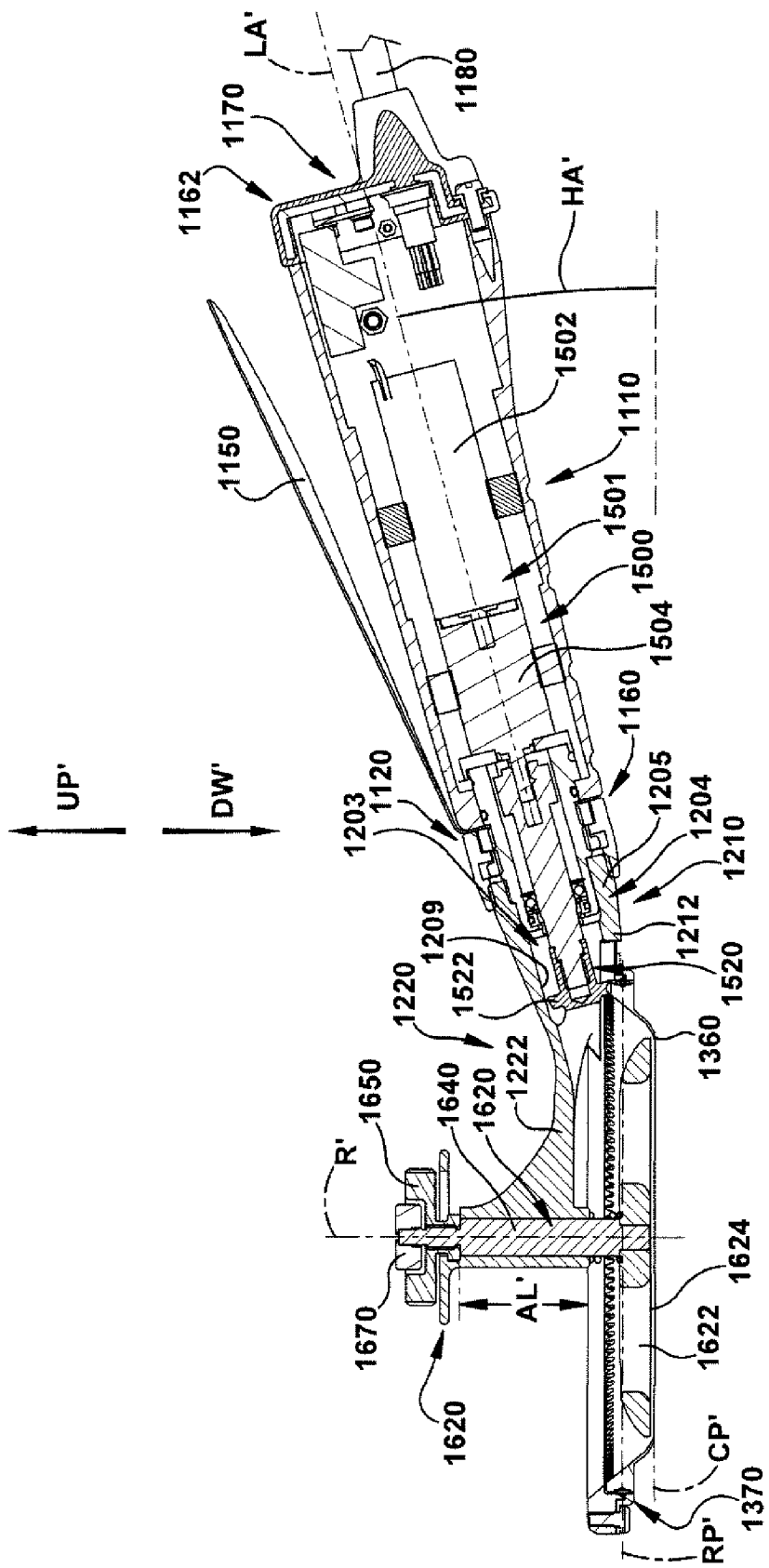
FIG. 24 is a schematic longitudinal section view of the power operated dermatome of FIG. 22, as viewed along a longitudinal axis LA' of the handle assembly of the dermatome and as seen from a plane indicated by the line 24-24 in FIG. 23.

A second exemplary embodiment of a hand-held, power operated dermatome of the present disclosure is schematically shown at 1000 in FIGS. 22-24. The power operated dermatome 1000 is similar in configuration and operation to the power operated dermatome 100, as described above, and the description of the dermatome 100, as set forth above, is referenced and incorporated herein with respect to the dermatome 1000.

The power operated dermatome includes an elongated handle assembly 1110, similar to the handle assembly 110, and a head assembly 1200, similar to the head assembly 200, extending from a forward or distal end 1160 of the handle assembly 1110. The handle assembly 1110 includes a handle 1112 and an actuation lever 1150 and extends between the distal end 1160 adjacent the head assembly 1200 and a proximal end 1162. A cover 1170 at the proximal end 1162 of the handle assembly 1110 is coupled to an air hose 1180 which provides motive power to the drive assembly 1500, similar to the drive assembly 500, of the dermatome 1000. An attachment assembly 1120, similar to the attachment assembly 120, releasably affixes the head assembly 1200 to the handle assembly 1110.

The dermatome 1000 includes the drive assembly 1500, similar to the drive assembly 500, including a drive motor assembly 1501, similar to the drive motor assembly 501, and a gear train 1520, similar to the gear train 520. The gear train 1520, in one exemplary embodiment, comprises a pinion gear 1522, similar to the pinion gear 522.

The head assembly 1200 includes a frame body or frame housing 1202, similar to the frame body 202, a rotary knife blade 1300, similar to the rotary knife blade 300, a blade housing assembly 1400, including a blade housing 1410 and a blade lock ring 1450, similar to the blade housing assembly 400, and a depth gauge assembly 1600, similar to the depth gauge assembly 600. The frame body 1202 includes a rearward handle attachment portion 1204 comprising a cylindrical body 1205 and a forward interface portion 1206. The frame body 1202 includes a gearbox housing 1203 defined by a throughbore 1209 through the frame body 1202. The gear train 1520 is supported within the gearbox housing 1203. The forward interface portion 1206 of the frame body 1202 includes a lower interface region 1210 that extends or transitions between the rearward handle attachment portion 1204 and the annular blade housing 1410 of the blade housing assembly 1400. The lower interface region 1210 includes a generally Y-shaped support 1212. The forward interface portion 1206 of the frame body 1202 also includes an upper interface region 1220 that extends or transitions between the rearward handle attachment portion 1204 and a central cylindrical support 1602 of the depth gauge assembly 1600. The upper interface region 1220 includes a generally V-shaped rib 1222 that converges proceeding toward and has a vertex generally at the central cylindrical support 1602.

The depth gauge assembly 1600 includes the depth gauge central cylindrical support 1602, similar to the central cylindrical support 602, that extends from the V-shaped rib 1222 of the upper interface region 1220 of the forward interface portion 1206 of the frame body 1202. The depth gauge assembly 1600 also includes a depth gauge 1620, similar to the depth gauge 620. The depth gauge 1620 includes the depth gauge shaft 1640 and a depth gauge plate 1622. The depth gauge assembly 1600 further includes a depth adjustment knob 1650 and a stop ring 1670, similar to the depth adjustment knob 650 and stop ring 670.

The rotary knife blade 1300 is supported for rotation about an axis of rotation R', similar to the axis of rotation R, by the blade housing assembly 1400. The rotary knife blade 1300 includes a cutting edge 1360 which defines a cutting plane CP', similar to the cutting plane CP, and further includes a continuous rolling bearing structure 1370, similar to the continuous rolling bearing structure 370, which defines a rotational plane RP' of the blade 1300, similar to the rotational plane RP of the blade 300. The blade housing assembly 1400 includes an annular blade housing 1410, similar to the blade housing 400, and a blade lock ring 450, similar to the blade lock ring 1450, which is releasably affixed to the blade housing 1410 to trap and secure the rotary knife blade 1300 for rotation with respect to the blade housing assembly 1400.

As can best be seen in FIG. 24, the handle assembly 1110 extends along a longitudinal axis LA' which is canted or angled upwardly at a handle angle HA' with respect to the cutting plane CP' and the rotational plane RP' of the rotary knife blade 1300 and with respect to the planar lower surface 1624 of the depth gauge plate 1622. That is, a proximal end 1162 of the handle assembly 1110 is spaced higher in an upward direction UP' above the cutting plane CP' of the rotary knife blade 1300 or the planar lower surface 1624 of the depth gauge plate 1622 than is the distal end 1160 of the handle assembly 1110. In the dermatome 100, the handle angle was substantially 0°. In one exemplary embodiment of the dermatome 1000, the handle angle HA' with respect to the cutting plane CP' or the rotational plane RP' of the rotary knife blade is in a range of 10°-20° and, more particularly, in one exemplary embodiment, the handle angle HA' may be approximately 15°. The handle angle HA' advantageously provides for ease of operation and clearance for the fingers of the operator. Recall that with the dermatomes 100, 1000 of the present disclosure, when excising a layer of skin tissue ST, the operator generally keeps the cutting plane CP' of the dermatome 1000 flush or flat against the surface SST of the skin tissue ST as the dermatome 1000 is moved along its path of travel PT. The upward angle HA' of the handle assembly 1110 of the dermatome 1000 facilitates keeping the cutting plane CP' of the dermatome head assembly 1200 flush or flat against the surface SST of the skin tissue ST during an excising procedure.

The rearward handle attachment portion 1204 of the frame body 1202 of the dermatome 1000 is slightly different than the corresponding rearward handle attachment portion 204 of the frame body 202 of the dermatome 100. To match the upward canted or tilted handle angle HA' of the handle assembly 1100, the rearward handle attachment portion 1204 is also angled upwardly to match the handle angle of the handle assembly 1100. This can best be seen in FIG. 24. Similarly, the gear train 1520 of the head assembly 1200 is modified accordingly to account for the different angle of contact between the pinion gear 1522 and the set of gear teeth of the rotary knife blade 1300.

Another difference between the dermatomes 100, 1000 involves an axial length of the respective depth gauge central cylindrical supports 602, 1602. To provide additional laterally stability and accuracy to the depth gauge plate 1622, in the dermatome 1000, an axial length AL' was increased slightly. Recall that the axial length AL of the cylindrical support 602 of the dermatome 100, in one exemplary embodiment, was approximately 1.05 in., while the overall axial length of the cylindrical support 602 extending between the upper end 604 of the cylindrical support 602 and the lower end 606 of the cylindrical support 602 was approximately 1.25 in. In one exemplary embodiment of the dermatome 100, the axial length AL' of the cylindrical support is approximately 1.30 in., while the overall axial length of the cylindrical support 1602 between the upper and lower ends is approximately 1.50 in.

Third Exemplary Embodiment-Power Operated Dermatome 2000

Figure 27:
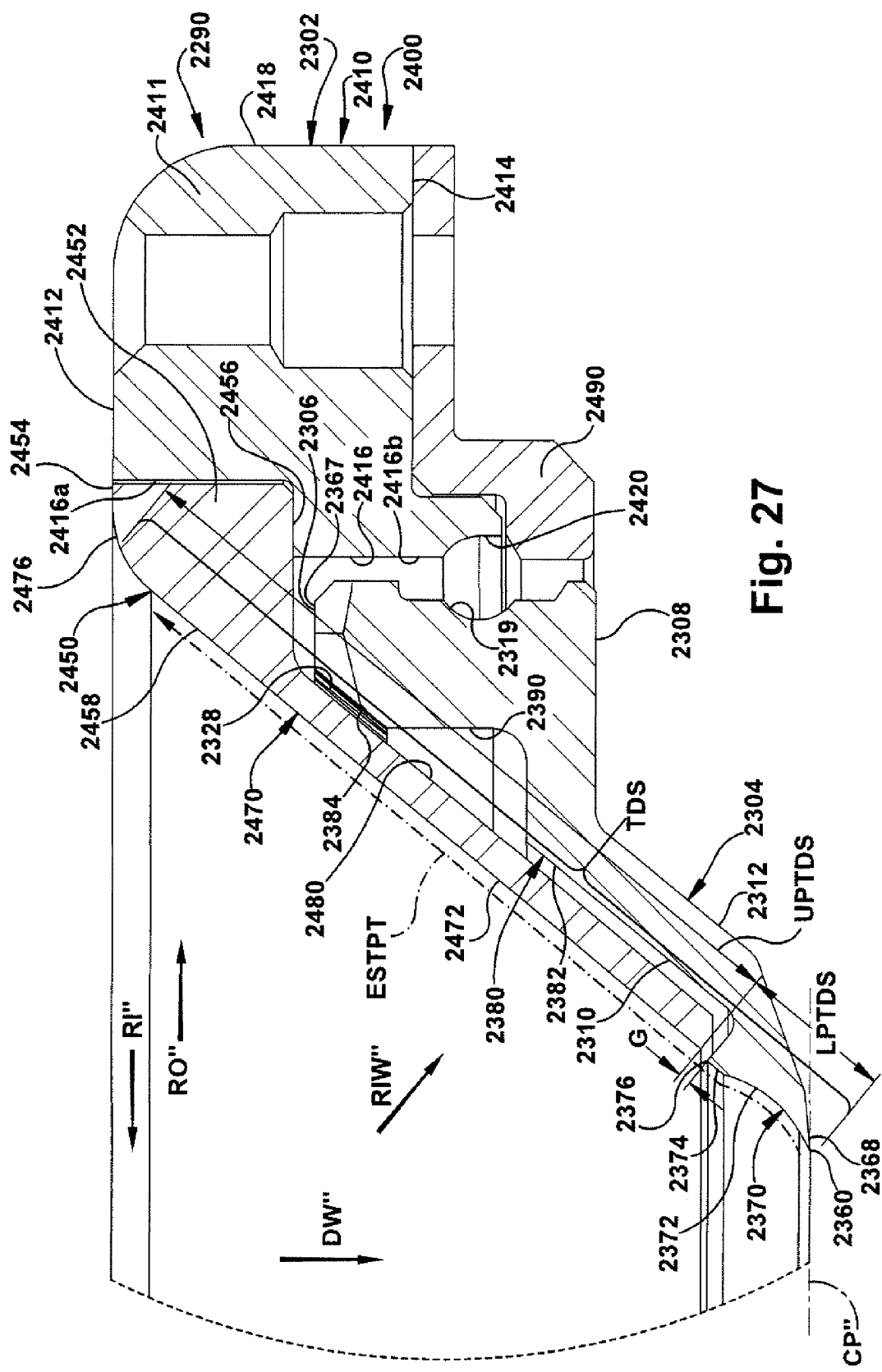
FIG. 27 is a schematic enlarged section view of a portion of the head assembly of FIG. 25 that is within a dashed circle labeled FIG. 27 in FIG. 26.

A third exemplary embodiment of a hand-held, power operated dermatome of the present disclosure is schematically shown at 2000 in FIGS. 25-27. Only a head assembly 2200 of the power operated dermatome 2000 is schematically illustrated in FIGS. 25-27, remainder of the power operated dermatome 2000, including the handle assembly and drive assembly, being similar in configuration and operation to the power operated dermatomes 100 and 1000, as described above. The descriptions of the dermatomes 100 and 1000, as set forth above, are referenced and incorporated herein with respect to the dermatome 2000.

The head assembly 2200 includes a depth gauge assembly 2600, including a depth gauge cylindrical support 2602. In the head assembly 2200, as depicted in FIGS. 25-27, parts of the depth gauge assembly 2600, including a depth gauge plate and a depth gauge shaft have been removed for clarity. The depth gauge assembly 2600 of the head assembly 2200 is similar in configuration and operation to the depth gauge assembly 1600 of the power operated dermatome 1000. The head assembly 2200 also includes a frame housing or body 2202, similar to the frame body 1202 of the power operated dermatome 1000. Like the frame body 1202 of the power operated dermatome 1000, a rearward handle attachment portion 2204 of the frame body 2202 of the dermatome 2000 is angled upwardly to match a handle angle of the handle assembly (not shown). Additionally, a continuous rolling bearing structure of the head assembly 2200, similar to the continuous rolling bearing structures 370, 1370 of the power operated dermatomes 100, 1000 has been removed from FIGS. 25-27 for clarity.

The head assembly 2200 of the present disclosure includes an annular rotary knife blade 2300, similar to the rotary knife blades 300, 1300 of the power operated dermatomes 100, 1000, supported for rotation by a blade housing assembly 2400 about a central axis of rotation R". The rotary knife blade 2300 defines a cutting plane CP''' substantially orthogonal to the rotary knife blade axis of rotation R". The head assembly 2200 also includes the blade housing assembly 2400 including a blade housing 2410 and a blade lock ring 2450, similar to blade housing assemblies 400, 1400 of the power operated dermatomes 100, 1000.

Rotary Knife Blade and Blade Housing Combination 2290

During certain tissue cutting operations with a power operated dermatome, excised skin tissue contacting an inner wall of the rotary knife blade may tend to rotate with the rotating knife blade, albeit at a much slower rotational velocity. That is, during certain tissue cutting operations, the excised skin tissue may tend to slide along the inner wall of the knife blade in the direction of blade rotation. Rotation of the excised skin tissue, even at a low rotational speed, is undesirable because the excised tissue could potentially wrap around the depth gauge plate and/or migrate into the pinion gear/knife blade interface region. To mitigate this potential problem, the section of excised skin tissue may be lifted with a pickup tool (i.e., tweezers) up and away from the blade cutting edge and the blade inner wall. However, if such an additional operation is required, either the operator must perform an additional task (use of the pickup tool) in addition to manipulating the power operated dermatome or an assistant would need to be provided to manipulate the pickup tool while the operator used the power operated dermatome. Both alternatives are generally not desirable.

Advantageously, the head assembly 2200 of the power operated dermatome 200 of the present disclosure addresses the potential problem of undesired excised tissue rotation. The head assembly 2200 includes a combination 2290 of an annular rotary knife blade 2300 and a blade housing assembly 2400. The blade housing assembly 2400 comprises a blade housing 2410 including a shield 2470 extending from a central body 2411 of the blade housing 2410 to and overlies a portion of an inner wall 2310 of the rotary knife blade 2300. The shield 2470, which is part of a blade housing cover 2450, is stationary and does not rotate with the rotary knife blade 2300. The shield 2470 defines a major part of an excised material-directing surface or tissue-directing surface TDS (FIG. 27) of the combination 2290 that extends from a cutting edge 2360 of the rotary knife blade 2300 to a first upper end 2412 of the blade housing 2410.

The material-directing surface or tissue-directing surface TDS receives the cut or excised skin tissue after being cut by the cutting edge 2360 of the rotary knife blade 2300 and directs the excised tissue upwardly and away from the cutting edge 2360 so as not to interfere with continued cutting. The inner wall 2310 of the rotary knife blade 2300 includes a raised, tissue-directing surface 2370 adjacent the cutting edge 2360. Advantageously, an inner surface 2472 of the shield 2470 is adjacent to and continues a tissue-directing surface 2370 of the inner wall 2310 of the rotary knife blade 2300. The stationary shield 2470 of the present disclosure advantageously mitigates the problem of rotation of the excised skin tissue by providing a stationary tissue-directing surface 2472 for receiving the excised skin tissue a very short distance after the tissue is cut by the cutting edge 2360 of the rotary knife blade 2300.

As can best be seen in FIG. 27, an extent of the total tissue directing surface TDS includes two components defined by two surfaces: a) a lower portion LPTDS of the tissue-directing surface TDS is defined by the lower tissue-directing surface 2370 of the rotary knife blade inner wall 2310; and b) an upper portion UPTDS of the tissue-directing surface TDS is defined by the tissue-directing inner surface 2474 of the shield 2470. The lower portion tissue-directing surface LPTDS is defined by the rotary knife blade 2300, thus, the lower portion of the tissue-directing surface LPTDS rotates with the knife blade 2300 at a high rotational speed. By contrast, the upper portion tissue-directing surface UPTDS is defined by the shield 2470 and is stationary, that is, the shield 2470, being affixed to the blade housing 2410, does not rotate with the rotary knife blade 2300.

As can best be seen in FIG. 27, the rotating, lower portion tissue-directing surface LPTDS defines a relatively small part of an overall extent of the tissue-directing surface TDS. In one exemplary embodiment, an extent of the lower portion tissue-directing surface LPTDS is on the order of 0.100-0.125 inch. By comparison, the stationary, upper portion tissue-directing surface UPTDS defines a relatively large extent of the overall extent of the tissue-directing surface TDS. In one exemplary embodiment, an extent of the upper portion tissue-directing surface UPTDS is on the order of 0.75-1.00 inch. Accordingly, during a tissue cutting operation with the power operated dermatome 2000 of the present disclosure, after cutting by the rotary knife blade cutting edge 2360, the excised tissue moves upwardly and away from the cutting edge 2360 along an excised skin tissue path of travel ESTPT (FIG. 27). By upwardly it is meant axially upwardly, that is, in the direction labeled UP in FIG. 25, by away it is meant radially away from the axis of rotation R" of the rotary knife blade 2300. The excised skin tissue path of travel ESTPT may be described as angled laterally upwardly with respect to the cutting plane CP" and the axis of rotation R" of the rotary knife blade 2300 since the path of travel ESTPT is a combination of an axially upwardly (the direction UP") with respect to the blade 2300 and radially away from the axis of rotation R" of the blade 2300. (Although shown in two dimensions as an arrow in section FIG. 27, it should be understood that the excised skin patent of travel ESTPT when viewed in three dimensions would have a width because the excised skin tissue sections have a width and the path of travel would generally conform to a section of a frustrum or frustoconical surface.) As the dermatome 2000 is manipulated during a tissue cutting operation, the excised skin tissue moves rapidly across the short, rotating tissue directing surface 2370 of the inner wall 2310 of the rotary knife blade 2300. The excised skin tissue is rapidly deposited on the inner surface 2472 of the shield 2470 where the excised skin tissue tends to gather or bunch up.

At any given time a length of excised skin tissue exposed to the rotational forces applied by the blade inner wall 2310 is limited to the extent of the lower portion tissue-directing surface LDTDS. Thus, in the combination 2290 of the present disclosure, contact between the excised skin tissue and the rotating rotary knife blade 2300 is advantageously minimized and the rotational forces applied by the rotary knife blade 2300 to the excised skin tissue section are also minimized by virtue of the stationary shield 2470. Stated another way, moving the excised skin tissue as short a distance as possible across the rotating lower portion tissue-directing surface LPTDS is desirable since this limits the rotational forces applied to the excised skin tissue by the rotating rotary knife blade 2300. Accordingly, in the combination 2290, the excised skin tissue is deposited on the stationary shield 2470 of the blade housing assembly 2400 with no external manipulation required or need for an assistant.

Rotary Knife Blade 2300

The rotary knife blade 2300 extends axially between a first, upper end 2367 and a second, lower end 2368 and includes an upper body section 2302 adjacent the upper end 2367 and a blade section 2304 adjacent the lower end 2368 of the blade 2300. The blade includes the inner wall 2310 and a radially spaced apart outer wall 2312. The inner wall 2310 defines an interior region 2301 that is generally frustoconical, converging in a direction proceeding toward the lower end 2368 of the blade 2300. The cutting edge 2360 of the blade 2300 is defined at an intersection of the lower end 2368 and the inner wall 2310. The body section 2302 of the blade extends axially between an upper end 2306 and a lower end 2308 and includes the driven gear 2328 (like the driven gear 328 of the rotary knife blade 300) defining the upper end 2367 of the blade and the upper end 2306 of the body section 2302. The body section 2302 defines a bearing surface 2319 (like the bearing surface 319 of the rotary knife blade 300) extending inwardly in the outer wall 2312. The body section 2302 of the rotary knife blade 2300 also includes a triangular-shaped (when viewed in cross section) cut out or notch region 2390 formed in the inner wall 2310.

Figure 28:
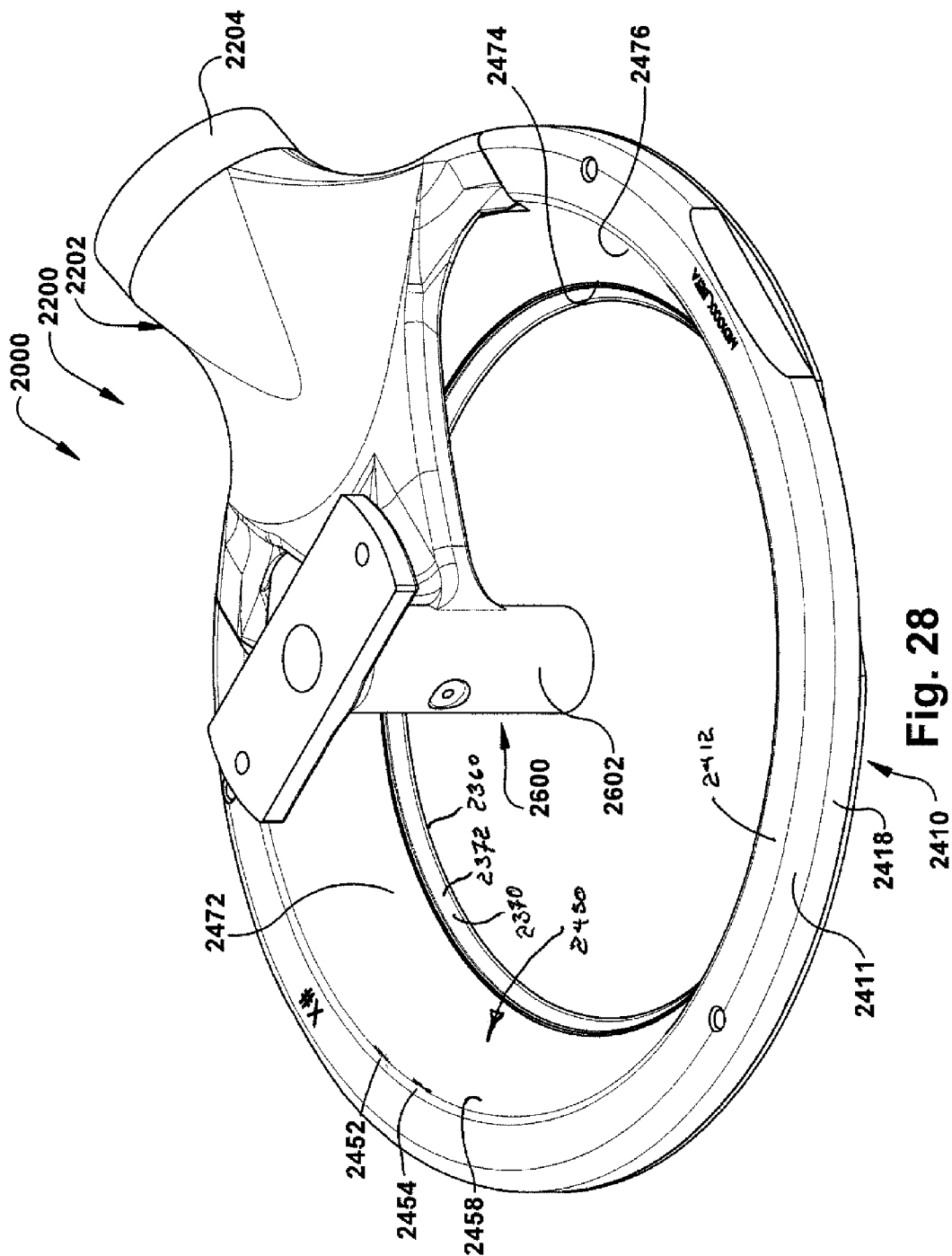
FIG. 28 is a schematic front perspective view of the head assembly of FIG. 25.

The blade section 2304 includes the cutting edge 2360 and the tissue-directing surface 2370 defined by the inner wall 2310 of the blade 2300 which is adjacent the cutting edge 2360. The tissue-directing surface 2370, which defines the lower portion tissue-directing surface LPTDS, includes a scalloped or arcuate concave portion 2372 adjacent the cutting edge 2360 and a ramped portion 2374 that provides a transition or ramp from the inner wall 2310 of the blade 2300 to the tissue-directing inner surface 2472 of the shield 2470 of the blade housing 2410, which defines the upper portion tissue-directing surface UPTDS. As can be seen in FIG. 28, for machining clearance purposes, there will be a slight gap G in the tissue-directing surface TDS along the excised skin tissue path of travel ESTPT between an upper end 2376 of the ramped portion 2374 and a lower end 2374 of the shield inner surface 2472.

The inner wall 2310 of the rotary knife blade 2300 further includes upper recessed portion 2380 extending between the upper end 2370*c* of the ramped portion 2370*b* and the upper end 2367 of the blade 2300. With respect to the inner wall 2310, the upper recessed portion 2380 is radially recessed or offset radially inwardly into the inner wall 2310 with respect to the portion of the inner wall 2310 defined by the raised tissue-directing surface 2370. That is, the upper recessed portion 2380 is generally located axially above the tissue-directing surface 2370 and further the upper recessed portion 2380 is radially offset inwardly into the inner wall 2310 from the tissue-directing surface 2370 as viewed along a direction labeled RIW" (radially into the inner wall 2350 of the rotary knife blade 2300) in FIG. 27. The direction labeled RIW" in FIG. 27 is generally orthogonal to a surface defined by the inner wall 2310 of the rotary knife blade 2300. Stated another way, if one considered a frustoconical surface defined by the upper recessed portion 2380 in three dimensions, that frustoconical surface would be radially spaced apart from a frustoconical surface defined by the tissue-directing surface 2370 in the direction RIW", that is, going radially into the inner wall 2310, as shown in FIG. 27. The direction RIW" is transverse to the axis of rotation R" and intersects the blade rotational plane RP".

The upper recessed portion 2380 includes a lower recessed region 2382, the notch region 2390 and an upper recessed region 2384. The lower recessed region 2382 is generally frustoconical and is recessed radially inwardly into the inner wall 2310 with respect to the upper end 2376 of the ramp portion 2374 of the tissue-directing surface 2370. The lower recessed region 2382 extends from the upper end 2376 of the ramp portion 2374 to the notch region 2390. The upper recessed region 2384 is also generally frustoconical and continues the frustoconical surface defined by the lower recessed region 2382. That is, the upper and lower recessed regions 2384, 2382 define a single frustoconical surface, which is interrupted by the notch region 2390.

The upper recessed portion 2380 of the inner wall 2310 includes and bridges both the body section 2302 and the blade section 2304 of the rotary knife blade 2300 and defines a channel, generally rectangular in cross section, that advantageously receives the shield 2470 such that the inner surface 2472 of the shield 2470 is adjacent to the upper end 2376 of the ramp portion 2374 of the tissue-directing surface 2374 of the inner wall 2310 of the rotary knife blade 2300 and such that the shield inner surface 2472 is axially and radially aligned with the tissue-direction surface 2372 of the rotary knife blade 2300. That is, the upper recessed portion 2380 of the inner wall 2310 is configured to provide a non-contacting seat or opening to receive the shield 2470 and allow for alignment of the tissue-direction surface 2372 of the rotary knife blade 2300 and the inner surface 2472 of the shield 2470 of the blade housing 2410 along the excised skin tissue path of travel ESTPT. This alignment forms a substantially continuous tissue-directing surface TDS from the cutting edge 2360 of the rotary knife blade 2300 to the upper end 2412 of the blade housing 2410. The tissue-directing surface TDS is continuous from the cutting edge 2360 of the rotary knife blade 2300 to the upper end 2412 of the blade housing 2410 except for the small discontinuity of gap G along the tissue-directing surface TDS between an upper end 2376 of the ramped portion 2374 and a lower end 2374 of the shield inner surface 2472 due to clearance required for manufacturing tolerance purposes.

Blade Housing Assembly 2400

The blade housing assembly 2400 includes the annular blade housing 2410, similar to the blade housings 410, 1410 of the power operated dermatomes 100, 1000, and a blade lock ring 2490, similar to the blade lock rings 450, 1450 of the power operated dermatomes 100, 1000. The blade housing 2410 and the lock ring 2490 are fastened together to secure the rotary knife blade 2300 for rotation, support by a continuous rolling bearing structure, similar to the continuous rolling bearing structure 370 of the dermatome. The functionality of the blade housing 2410 and the lock ring 2490, together with the rolling bearing structure (not shown in FIGS. 25-27, are similar to the corresponding structures described with respect to the dermatomes 100, 1000 and, for brevity, will not be repeated.

The blade housing 2410 includes the central body 2411 which is positioned generally axially upwardly from and radially outwardly of the rotary knife blade 2300 and includes the first, upper end 2412 and an axially spaced apart second, lower end 2414. The blade housing 2410 further includes an inner wall 2416 and a radially spaced apart outer wall 2418. The inner wall 2416 includes an upper portion 2416a adjacent the upper end 2412 and a stepped lower portion 2416b adjacent the lower end 2414. The lower portion 2416b includes a bearing surface 2420 adjacent the lower end 2414, similar to the bearing surface 420 of the power operated dermatome 100.

As can best be seen in FIG. 27, the upper portion 2416a of the inner wall 2416 of the blade housing 2410 is positioned axially above the upper end 2367 of the rotary knife blade 2300. The blade housing cover 2450, which is part of the blade housing 2410, extends radially inwardly (that is, in a direction toward the axis of rotation R" of the rotary knife blade 2300, shown as RI" in FIG. 27) from the upper portion 2416a of the inner wall. The blade housing cover 2450 may be fabricated as integral with the blade housing 2410 or as a separate component which is permanently affixed to the blade housing 2410, for example, by welding. The blade housing cover 2450 includes a base 2452 which is generally triangular in cross section. The base 2452 is positioned axially above and the upper end 2367 of the rotary knife blade 2300. The base 2452 defines an upper end 2454 and an axially space apart lower end 2456. The upper end 2454 of the blade housing cover 2450 is aligned with and defines a portion of the upper surface 2412 of the blade housing 2410. The base 2452 includes an inner surface 2458 which defines a portion of and is part of the tissue-directing inner surface 2472 of the shield 2470. That is, the tissue-directing inner surface 2472 of the shield 2470 extends from the lower end 2474 of the inner surface 2472 to an upper transition region 2476 adjacent the upper end 2454 of the base 2452 and thus includes the base inner surface 2458.

Extending at an angle radially inwardly RI" and downwardly (direction DW" in FIG. 27) is the shield 2470. The shield 2470 is generally rectangular in cross section and, in three dimensions, the shield 2470 is generally frustoconical in shape, following the general contours of the frustoconical upper and lower regions 2384, 2382 of the upper recessed portion 2380 of the inner wall 2310 of the blade 2300. The shield 2370 includes the tissue-directing inner surface 2472 and a radially space apart outer surface 2480. The shield 2470 is received in and extends along the upper recessed portion 2380 of the inner wall 2310 of the rotary knife blade 2300. The shield 2470 is sized to fit in the upper recessed portion 2380 such that the inner surface 2472 of the shield 2470 is in proximity and adjacent to, aligned with and continues the tissue-directing surface 2370 of the rotary knife blade inner wall 2310. The shield inner surface 2472 defines a portion of the excised skin tissue path of travel ESTPT and defines the upper portion UPTDS of the substantially continuous tissue-directing surface TDS of the blade-blade housing combination 2290.

The lower end 2474 of the inner surface 2472 of the shield is spaced slightly radially outwardly RO" (FIG. 27) of the upper end 2376 of the ramp portion 2374 of the tissue-directing surface 2370 of the inner wall 2310 of the rotary knife blade 2300 to mitigate the possibility of excised tissue entering the small gap G between the rotary knife blade 2300 and the shield 2470 as the excised tissue flows along the excised skin tissue path of travel ESTPT. The outer surface 2480 of the shield 2470 is in proximity to but spaced from the facing surfaces of the upper and lower regions 2384, 2382 of the upper recessed portion 2380 of the inner wall 2310 of the blade 2300. That is, the blade housing cover 2450 overlies but does not contact the facing surfaces of the rotary knife blade 2300.

Figure 29:
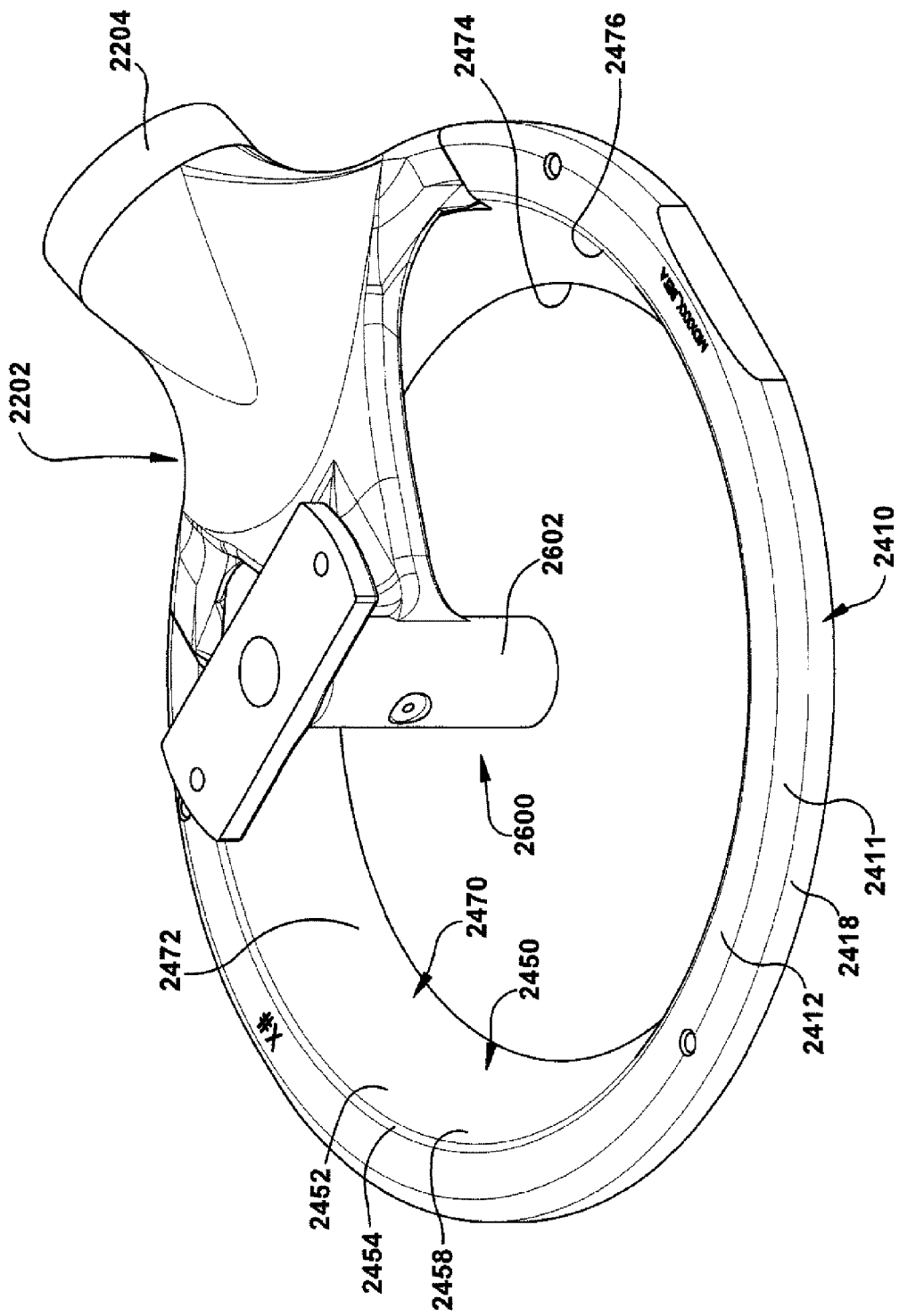
FIG. 29 is a schematic front perspective view of the head assembly of FIG. 25 with a rotary knife blade and a blade lock ring of a blade housing assembly removed.
Figure 30:
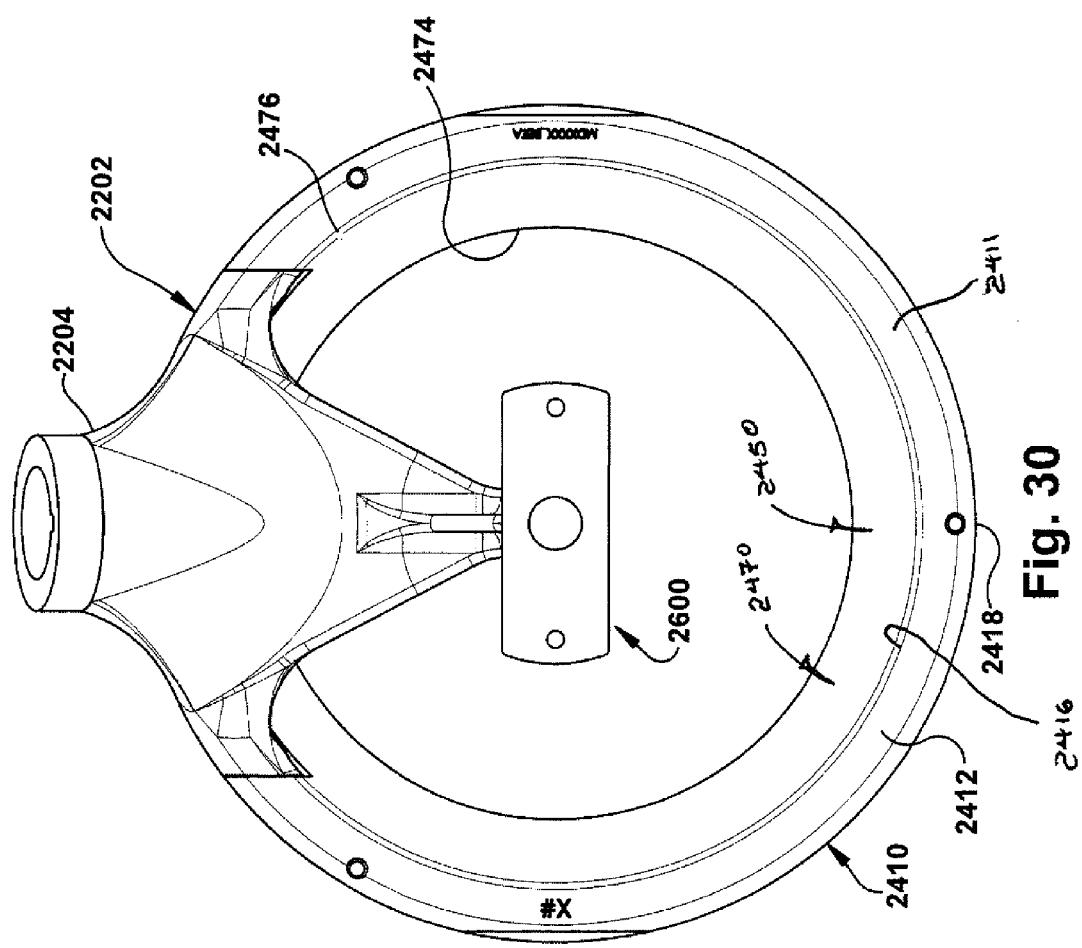
FIG. 30 is a schematic top plan view of the head assembly of FIG. 25 with a rotary knife blade and a blade lock ring of a blade housing assembly removed.

As can best be seen in FIGS. 29-31, which schematically depict the head assembly frame body 2202 and the blade housing 2410, with the rotary knife blade 2300 and the blade lock ring 2490 of the blade housing assembly 2400 removed for clarity, the blade housing cover 2450, including the shield 2470, extends about the entirety of a 360° circumference of the blade housing 2410. That is, no matter what angular section of the rotary knife blade 2300 is used in a cutting or trimming operation, the shield 2470 is positioned with respect to the tissue-directing surface 2370 of the rotary knife blade 2300 such that the inner surface 2472 of the shield 2470m defining the upper portion tissue-directing surface UPTDS, is adjacent to and aligned with the raised tissue-directing surface 2370 of the rotary knife 2300, defining the lower portion tissue-directing surface LPTDS, so as to form a substantially continuous total tissue-directing surface TDS extending from the cutting edge 2360 of the blade 2300 to the upper end 2412 of the blade housing 2410.

It should be understood that the power operated dermatomes of the present disclosure, including the power operated dermatome 2000 may be used for trimming and cutting various materials, in addition to cutting or excising of skin tissue. Accordingly, references in this application, including the claims, to tissue, skin tissue, excised skin tissue, excised skin tissue path of travel, tissue-directing surface, etc. should be understood to apply equally to any material, be it tissue, skin tissue or otherwise, cut or trimmed by the dermatome 2000. Thus, references to tissue, skin tissue, excised skin tissue path of travel, tissue-directing surface, etc. are to be understood broadly to include or refer to any material suitable for cutting or trimming by the power operated dermatomes of the present disclosure, including the power operated dermatome 2000.

As used herein, terms of orientation and/or direction such as front, rear, forward, rearward, distal, proximal, distally, proximally, upper, lower, inward, outward, inwardly, outwardly, horizontal, horizontally, vertical, vertically, axial, radial, longitudinal, axially, radially, longitudinally, etc., are provided for convenience purposes and relate generally to the orientation shown in the Figures and/or discussed in the Detailed Description. Such orientation/direction terms are not intended to limit the scope of the present disclosure, this application, and/or the invention or inventions described therein, and/or any of the claims appended hereto. Further, as used herein, the terms comprise, comprises, and comprising are taken to specify the presence of stated features, elements, integers, steps or components, but do not preclude the presence or addition of one or more other features, elements, integers, steps or components.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A combination of an annular rotary knife blade and a blade housing assembly for a power operated dermatome, the blade housing assembly supporting the annular rotary knife blade for rotation with respect to the blade housing assembly, the combination comprising: the annular rotary knife blade supported for rotation about an axis of rotation by the blade housing assembly, the annular rotary knife blade including a first end and an axially spaced apart second end and an inner wall and a radially spaced apart outer wall, the second end defining a cutting edge, the inner wall defining an interior region of the annular rotary knife blade and including a lower material-directing surface adjacent the cutting edge and a radially recessed upper portion; and the blade housing assembly including a blade housing having a first upper end and an axially spaced apart second lower end and an inner wall and a radially spaced apart outer wall, the first end of the annular rotary knife blade positioned between the first upper end and the second lower end of the blade housing as viewed with respect to the axis of rotation of the annular rotary knife blade, and a blade housing cover extending from the blade housing into the interior region of the annular rotary knife blade, the blade housing cover including a shield extending along the radially recessed upper portion of the annular rotary knife blade inner wall and having an inner surface adjacent to and continuing the lower material-directing surface of the annular rotary knife blade inner wall, a lower end of the inner surface of the shield extending below the second lower end of the blade housing adjacent the outer wall of the blade housing.

2. The combination of claim 1 wherein the shield of the blade housing cover extends into the radially recessed upper portion of the annular rotary knife blade inner wall.

3. The combination of claim 1 wherein the blade housing assembly includes a blade lock ring removably attached to the blade housing to secure the rotary knife blade to the blade housing assembly.

4. A combination of a rotary knife blade and a blade housing assembly for a power operated dermatome, the blade housing assembly supporting the rotary knife blade for rotation about an axis of rotation with respect to the blade housing assembly and the combination defining a material-directing surface for tissue cut by the rotary knife blade, the combination comprising: the rotary knife blade including a first end and an axially spaced apart second end and an inner wall and a radially spaced apart outer wall, the second end having a cutting edge defining a cutting plane substantially orthogonal to the axis of rotation, the inner wall defining an interior region of the rotary knife blade and including a material-directing surface adjacent the cutting edge and a radially-recessed upper portion; and the blade housing assembly including a blade housing having a first upper end and an axially spaced apart second lower end and an inner wall and a radially spaced apart outer wall, the first end of the rotary knife blade positioned between the first upper end and the second lower end of the blade housing as viewed with respect to the axis of rotation of the rotary knife blade, and a blade housing cover extending from the blade housing into the interior region of the rotary knife blade, the blade housing cover including a shield extending along the radially recessed upper portion of the rotary knife blade inner wall and having a material-directing inner surface adjacent to and continuing the material-directing surface of the rotary knife blade inner wall, the material-directing surface of the rotary knife blade and the material-directing inner surface of the blade housing cover shield comprising the material-directing surface of the combination, a lower end of the material-directing inner surface of the shield extending below the second lower end of the blade housing adjacent the outer wall of the blade housing.

5. The combination of claim 4 wherein the shield of the blade housing cover extends into the radially recessed upper portion of the rotary knife blade inner wall.

6. The combination of claim 4 wherein the blade housing assembly includes a blade lock ring removably attached to the blade housing to secure the rotary knife blade to the blade housing assembly.

7. A head assembly for a power operated dermatome, the head assembly comprising: a frame body supporting a gear train, an annular rotary knife blade, a blade housing assembly supporting the annular rotary knife blade for rotation about an axis of rotation with respect to the blade housing assembly, the annular rotary knife blade including a first end and an axially spaced apart second end and an inner wall and a radially spaced apart outer wall, the second end defining a cutting edge, the inner wall defining an interior region of the annular rotary knife blade and including a lower material-directing surface adjacent the cutting edge and a radially recessed upper portion; and the blade housing assembly including a blade housing having a first upper end and an axially spaced apart second lower end and an inner wall and a radially spaced apart outer wall, the first end of the annular rotary knife blade positioned between the first upper end and the second lower end of the blade housing as viewed with respect to the axis of rotation of the annular rotary knife blade, and a blade housing cover extending from the blade housing into the interior region of the annular rotary knife blade, the blade housing cover including a shield extending along the radially recessed upper portion of the annular rotary knife blade inner wall and having an inner surface adjacent to and continuing the lower material-directing surface of the rotary knife blade inner wall, a lower end of the inner surface of the shield extending below the second lower end of the blade housing adjacent the outer wall of the blade housing.

8. The head assembly of claim 7 wherein the shield of the blade housing cover extends into the radially recessed upper portion of the annular rotary knife blade inner wall.

9. The head assembly of claim 7 wherein the blade housing assembly includes a blade lock ring removably attached to the blade housing to secure the annular rotary knife blade to the blade housing assembly.

10. A combination of a power driven rotary knife blade and a blade housing assembly supporting the power driven rotary knife blade for rotation with respect to the blade housing assembly, the combination comprising: the power driven rotary knife blade supported for rotation about an axis of rotation by the blade housing assembly, the power driven rotary knife blade including a first end and an axially spaced apart second end and an inner wall and a radially spaced apart outer wall, the second end defining a cutting edge, the inner wall defining an interior region of the power driven rotary knife blade and including a lower material-directing surface adjacent the cutting edge and a radially recessed upper portion; and the blade housing assembly including a blade housing having a first upper end and an axially spaced apart second lower end and an inner wall and a radially spaced apart outer wall, the first end of the power driven rotary knife blade positioned between the first upper end and the second lower end of the blade housing as viewed with respect to the axis of rotation of the power driven rotary knife blade, and a blade housing cover extending from the inner wall of the blade housing into the interior region of the power driven rotary knife blade, the blade housing cover including a shield extending along the radially recessed upper portion of the power driven rotary knife blade inner wall and having an inner surface adjacent to and aligned with the lower material-directing surface of the power driven rotary knife blade inner wall, a lower end of the inner surface of the shield extending below the second lower end of the blade housing.

11. The combination of claim 10 wherein the shield of the blade housing cover extends into the radially recessed upper portion of the power driven rotary knife blade inner wall.

12. The combination of claim 10 wherein the blade housing assembly includes a blade lock ring removably attached to the blade housing to secure the power driven rotary knife blade to the blade housing assembly.

13. A power operated dermatome comprising: a rotary knife blade including a first end and an axially spaced apart second end and an inner wall and a radially spaced apart outer wall, the second end defining a cutting edge, the inner wall defining an interior region of the rotary knife blade and including a lower material-directing surface adjacent the cutting edge and a radially recessed upper portion; and a blade housing assembly supporting the rotary knife blade for rotation with respect to the blade housing assembly, the blade housing assembly including a blade housing having a first upper end and an axially spaced apart second lower end and an inner wall and a radially spaced apart outer wall, the first end of the rotary knife blade positioned between the first upper end and the second lower end of the blade housing as viewed with respect to an axis of rotation of the rotary knife blade, and a blade housing cover extending from the inner wall of the blade housing into the interior region of the rotary knife blade, the blade housing cover including a shield extending along the radially recessed upper portion of the rotary knife blade inner wall and having an inner surface adjacent to and aligned with the lower material-directing lower surface of the rotary knife blade inner wall, a lower end of the inner surface of the shield extending below the second lower end of the blade housing.

14. The power operated dermatome of claim 13 wherein the shield of the blade housing cover extends into the radially recessed upper portion of the rotary knife blade inner wall.

15. The power operated dermatome of claim 13 wherein the blade housing assembly includes a blade lock ring removably attached to the blade housing to secure the rotary knife blade to the blade housing assembly.

16. The combination of claim 1 wherein a lower portion of the inner wall of the blade housing includes a bearing surface extending radially inwardly into the inner wall.

17. The combination of claim 4 wherein a lower portion of the inner wall of the blade housing includes a bearing surface extending radially inwardly into the inner wall.

18. The head assembly of claim 7 wherein a lower portion of the inner wall of the blade housing includes a bearing surface extending radially inwardly into the inner wall.

19. The combination of claim 10 wherein a lower portion of the inner wall of the blade housing includes a bearing surface extending radially inwardly into the inner wall.

20. The power operated dermatome of claim 13 wherein a lower portion of the inner wall of the blade housing includes a bearing surface extending radially inwardly into the inner wall.

21. A combination of an annular rotary knife blade and a blade housing assembly for a power operated dermatome, the blade housing assembly supporting the annular rotary knife blade for rotation with respect to the blade housing assembly, the combination comprising: the annular rotary knife blade supported for rotation about an axis of rotation by the blade housing assembly, the annular rotary knife blade including a first end and an axially spaced apart second end and an inner wall and a radially spaced apart outer wall, the second end defining a cutting edge, the inner wall defining an interior region of the annular rotary knife blade and including a lower material-directing surface and a recessed upper portion; and the blade housing assembly including a blade housing and a blade lock ring coupled to the blade housing, the blade housing having a first upper end and an axially spaced apart second lower end and an inner wall and a radially spaced apart outer wall, the first end of the annular rotary knife blade positioned between the first upper end and the second lower end of the blade housing as viewed with respect to the axis of rotation of the annular rotary knife blade, the blade housing including a blade housing cover extending from the blade housing into the interior region of the annular rotary knife blade, the blade housing cover including a shield extending along the recessed upper portion of the annular rotary knife blade inner wall and having an inner surface adjacent to and continuing the lower material-directing surface of the annular rotary knife blade inner wall, the blade lock ring including an inner surface and a radially spaced apart outer surface and an upper surface and an axially spaced apart lower surface, the inner surface of the blade lock ring including a bearing surface adjacent the upper surface of the blade lock ring, the blade housing including a bearing surface extending axially upwardly into a second lower end of the blade housing, the bearing surface of the blade lock ring and the bearing surface of the blade housing in axial alignment defining a bearing race of the blade housing assembly.

22. The combination of an annular rotary knife blade and a blade housing assembly of claim 21 wherein the bearing surface of the blade housing comprises an arcuate bearing surface and the bearing surface of the blade lock ring comprises an arcuate bearing surface.

23. A combination of a power driven rotary knife blade and a blade housing assembly supporting the power driven rotary knife blade for rotation with respect to the blade housing assembly, the combination comprising: the power driven rotary knife blade supported for rotation about an axis of rotation by the blade housing assembly, the power driven rotary knife blade including a first end and an axially spaced apart second end and an inner wall and a radially spaced apart outer wall, the second end defining a cutting edge, the inner wall defining an interior region of the power driven rotary knife blade and including a lower material-directing surface adjacent the cutting edge and a radially recessed upper portion; and the blade housing assembly including a blade housing having a central body including a first end and an axially spaced apart second end and an inner wall and a radially spaced apart outer wall, the first end of the power driven rotary knife blade positioned between the first end of the central body of the blade housing and the second end of the central body of the blade housing as viewed with respect to the axis of rotation of the power driven rotary knife blade, the blade housing including a blade housing cover extending from the inner wall of the central body of the blade housing into the interior region of the power driven rotary knife blade, the blade housing cover including a shield extending along the radially recessed upper portion of the power driven rotary knife blade inner wall and having an inner surface adjacent to and continuing the lower material-directing surface of the power driven rotary knife blade inner wall, a lower end of the inner surface of the shield extending below the second end of the central body of the blade housing adjacent the outer wall of the central body of the blade housing.

24. A power operated dermatome comprising: a rotary knife blade including a first end and an axially spaced apart second end and an inner wall and a radially spaced apart outer wall, the second end defining a cutting edge, the inner wall defining an interior region of the rotary knife blade and including a lower material-directing surface adjacent the cutting edge and a radially recessed upper portion; and a blade housing assembly supporting the rotary knife blade for rotation with respect to the blade housing assembly, the blade housing assembly including a blade housing having a central body including a first end and an axially spaced apart second end and an inner wall and a radially spaced apart outer wall, the first end of the rotary knife blade positioned between the first end of the central body of the blade housing and the second end of the central body of the blade housing as viewed with respect to the axis of rotation of the rotary knife blade, the blade housing including a blade housing cover extending from the inner wall of the blade housing into the interior region of the rotary knife blade, the blade housing cover including a shield extending along the radially recessed upper portion of the rotary knife blade inner wall and having an inner surface adjacent to and continuing the lower material-directing lower surface of the rotary knife blade inner wall, a lower end of the inner surface of the shield extending below the second end of the central body of the blade housing adjacent the outer wall of the central body of the blade housing.

\* \* \* \* \*